US008280488B2

(12) United States Patent
Huisman et al.

(10) Patent No.: US 8,280,488 B2
(45) Date of Patent: Oct. 2, 2012

(54) PROCESSING AND DISPLAYING DYNAMIC CONTRAST-ENHANCED MAGNETIC RESONANCE IMAGING INFORMATION

(76) Inventors: Henkjan J. Huisman, Nijmegen (NL); Nico Karssemeijer, Beek (NL)

( * ) Notice: Subject to any disclaimer, the term of this patent is extended or adjusted under 35 U.S.C. 154(b) by 933 days.

(21) Appl. No.: 11/604,083

(22) Filed: Nov. 24, 2006

(65) Prior Publication Data

US 2008/0125643 A1    May 29, 2008

Related U.S. Application Data

(60) Provisional application No. 60/867,164, filed on Nov. 24, 2006.

(51) Int. Cl.
 *A61B 5/055* (2006.01)
(52) U.S. Cl. ..................... 600/420; 600/407
(58) Field of Classification Search .............. 600/407, 600/410, 416, 420, 431
 See application file for complete search history.

(56) References Cited

U.S. PATENT DOCUMENTS

| 6,611,778 | B2 | 8/2003 | Degani | |
|---|---|---|---|---|
| 2004/0242994 | A1* | 12/2004 | Brady et al. | 600/420 |
| 2007/0203412 | A1* | 8/2007 | Sugiura | 600/410 |

OTHER PUBLICATIONS

Strecker, R.,et. al., "DCE-MRI in Clinical Trials: Data Acquisition Techniques and Analysis Methods," Intl. Jrnl. Clin. Pharm. Therapeutics Abstracts, vol. 41, 2003, pp. 603-605.
Tofts, P., et. al., "Estimating Kinetic Parameters from Dynamic Contrast-Enhanced . . . Diffusable Tracer:Std. Quant. and Symbols," Jrnl. Mag. Res. Img., vol. 10, 1999, pp. 223-232.
Yang, C., et. al.,"Estimating the Arterial Input Function Using Two Reference Tissues in Dynamic Contrast-Enhanced MRI Studies," Magn. Res. in Med. vol. 52, 2004, pp. 1110-1117.
Huisman, H., et. al., "Effect of Calibration on Classification of Lesions . . . Using Pharmacokenetic Model.," presented Dec. 1, 2005 Radiol. Soc. of North America (RSNA) Conference.
Bartella, L., et. al., "Proton MR Spectroscopy with Choline Peak . . . for Breast Cancer Diagnosis: Preliminary Study," Radiology, vol. 239, No. 3, 2006, pp. 686-692.
Shah, N., et. al., "Magnetic Resonance Spectroscopy as Imaging Tool for Cancer: A Review of the Literature," JAOA Student Contribution, vol. 106, No. 1, Jan. 2006, pp. 23-27.
Stalsett, Eli, "In Vivo Mapping of Tumor Microcirculation Parameters Using . . . Enhanced MRI," Thesis for Degree in Experimental and Human Physiology, 2004, Univ. Bergen, Norway.
Freer, T., et. al.,"Screening Mammography with Computer-Aided Detection: Prospective Study . . . in a Community Breast Center," Radiology, vol. 220, No. 3, 2001, pp. 781-786.

(Continued)

*Primary Examiner* — Tse Chen
*Assistant Examiner* — Rochelle Reardon
(74) *Attorney, Agent, or Firm* — William L. Wang

(57) ABSTRACT

A method, system, and related computer program products for processing and displaying dynamic contrast-enhanced magnetic resonance imaging (DCE-MRI) information are described. A plurality of instances of an MRI volume of the body part acquired at a respective plurality of sample times subsequent to an administration of a tracer is processed to determine a plurality of pharmacokinetic (PK) parameters characterizing a mathematical model-based relationship between a plasma tracer concentration and a total tracer concentration within the body part. For one preferred embodiment, computation of the PK parameters is performed according to a generalized signal model such that computation can be carried out in real time during an interactive viewer session, with required reference regions being selectable and optionally re-selectable by the viewer without requiring extensive waiting times for PK parameter computation. Associated user interfaces and computer-aided detection (CAD) algorithms are also provided.

20 Claims, 19 Drawing Sheets

OTHER PUBLICATIONS

Futterer, J., et. al., "Prostate Cancer Localization with Dynamic Contrast-Enhanced MRI and Proton MR Spectroscopic Imaging," Radiology, vol. 241, No. 2, 2006, pp. 449-458.

Gilhuijs, K., et. al., "Breast MR Imaging in Women at Increased Lifetime Risk of Breast Cancer: Clinical System . . . Initial Results," Radiology, vol. 225, No. 3, 2002, pp. 907-916.

Gilhuijs, K., et. al., "Computerized Analysis of Breast Lesions in Three Dimensions Using Dynamic MRI," Med. Phys., vol. 25, No. 9, 1998, pp. 1647-1654.

Huisman, H., et. al., "Accurate Estimation of Pharmacokinetic Contrast-Enhanced Dynamic MRI Param. of the Prostate," Jrnl. Mag. Reson. Imag., vol. 13, No. 4, 2001, pp. 607-614.

Huisman, H., et. al., "Prostate Cancer: Precision of Integrating Functional MRI . . . Using Fiducial Gold Markers," Radiology, vol. 236, No. 1, 2005, pp. 311-317.

Kovar, D., et. al., "A New Method for Imaging Perfusion and Contrast Extraction Fraction: Input . . . from Ref. Tissues," Jrnl. Mag. Reson. Imag., vol. 8, No. 5, 1998, pp. 1126-1134.

Kriege, M., et. al., "Efficacy of MRI and Mammography for Breast-Cancer Screening in Women with . . . Predisposition," N. Engl. Jrn. Med., vol. 351, No. 5, 2004, pp. 427-437.

Leach, M., et. al., "Screening with MRI and Mammography of a UK Population . . . A Prospective Multicentre Cohort Study (MARIBS)," The Lancet, vol. 365, No. 9473, 2005, pp. 1769-1778.

Liberman, L., et. al., "MRI Findings in the Contralateral Breast of Women with Recently Diagnosed Breast Cancer," AJR Am. J. Roentgenol, vol. 180, No. 2, 2003, pp. 333-341.

Sardanelli, F., et. al., "Sensitivity of MRI versus Mammography . . . using the Whole-Breast Pathologic Exam. as Gold Standard," AJR, vol. 183, No. 4, Oct. 2004, pp. 1149-1157.

Warner, E., et. al., "Surveillance of BRCA1 and BRCA2 Mutation Carriers with MRI, Ultrasound, . . . and Clinical Breast Exam.," JAMA, vol. 292, No. 11, Sep. 15, 2004, pp. 1317-1325.

Kuhl, C., et. al., "Breast MRI Screening in 192 Women . . . Carriers of Breast Cancer Susceptibility Gene:Prelim. Results," Radiology, vol. 215, Apr. 2000, pp. 267-279.

Kriege, M., et. al., "Differences between First and Subsequent Rounds of the MRISC Breast Cancer Screening Program for Women . . . Predisposition," Cancer, 2006, pp. 2318-2326.

Stoutjeskijk, M., et. al., "MRI and Mammography in Women with Hereditary Risk of Breast Cancer," Jrnl. Natl. Cancer Inst., vol. 93, 2001, pp. 1095-1102.

Port, R., et. al., "Dynamic Contrast-Enhanced MRI using Gd-DTPA: . . . for the Assessment of Kinetics in Tumors," Magn. Reson. Med., vol. 45, 2001, pp. 1030-1038.

Jain, A., "Fundamentals of Digital Image Processing," Prentice-Hall, 1989.

Brix, G., et. al., "Pharmacokinetic Parameters in CNS Gd-DTPA Enhanced MRI," Jrnl. Comput. Asst. Tomogr., vol. 15, 1991, pp. 621-628.

Hittmair, K., et. al., "Method for Quantitative Assessment of Contrast Agent Uptake in Dyn. Contrast-Enhanced MRI," Magn. Reson. Med., vol. 31, 1994, pp. 567-571.

Rutter, C., "Bootstrap Estimation of Diagnostic Accuracy with Patient-Clustered Data," Acad Radiol 2000, vol. 7, pp. 413-419.

Ostergaard L, et. al., High Resolution Measurement of Cerebral Blood Flow Using Intravascular Tracer Bolus Passages. Part 1: Math Appr., Magn Res in Med, 1996, V.36 pp. 715-725.

Koh, T., et. al., "Assessment of Perfusion by Dynamic Contrast-Enhanced Imaging using a Deconvolution Approach . . . ," IEEE Trans. Med. Imaging, vol. 23, 2004, pp. 1532-1542.

Luo, Y., et. al., "BISTRO: An Outer-Volume Suppression Method that Tolerates RF Field Inhomogeneity," Magnetic Resonance in Medicine, 2001, vol. 45, pp. 1095-1102.

\* cited by examiner

PROCESSING AND DISPLAYING DYNAMIC CONTRAST-ENHANCED MAGNETIC RESONANCE IMAGING INFORMATION

CROSS-REFERENCE TO RELATED APPLICATIONS

The subject matter of this patent application is related to the subject matter of U.S. Provisional Application No. 60/867,164, which was filed on the same day as this patent application (Nov. 24, 2006), and which is incorporated by reference herein.

FIELD

This patent specification relates to medical imaging. More particularly, this patent specification relates to the processing and/or display of information associated with a dynamic contrast-enhanced magnetic resonance imaging (DCE-MRI) process.

BACKGROUND

Dynamic contrast-enhanced magnetic resonance imaging (DCE-MRI) represents one promising tool in the fight against breast cancer, prostate cancer, and other cancer types. In DCE-MRI, a contrast agent known to significantly and predictably enhance certain MRI readings, such as T1-weighted MRI readings, is injected into the patient and a time sequence of MRI volumes is acquired. As the contrast agent, commonly termed a tracer, is transported throughout the body by the vascular system (e.g., arteries, arterioles, capillaries, veins, and other types of blood vessels), it diffuses across the vessel walls into the surrounding tissue. The surrounding tissue generally comprises (i) tissue cells and (ii) interstitial space among the tissue cells, termed extracellular extravascular space (EES). The tracer, which in one example comprises gadolinium and diethylenetriamine penta-acetic acid (Gd-DTPA), is selected such that it "washes into" the EES by diffusion across the vessel walls but does not enter the tissue cells.

Initially, the tracer "washes into" the EES because its concentration is higher inside the vessel walls (i.e., in the blood plasma) than outside the vessel walls (i.e., in the EES). However, as the concentration of the tracer in the blood plasma becomes increasingly diluted, it reaches a point where the tracer concentration in the blood plasma becomes less than in the EES, after which the tracer begins to "wash out" from the EES by diffusing across the vessel walls back into the blood plasma. It has been found that local tissue characteristics, including characteristics that may be associated with cancer or other tissue abnormalities, can highly affect the particular local time dynamics of the tracer wash-in and wash-out processes. Qualitative visual study of the time sequence of MRI volumes can yield some insight into such local tissue characteristics. However, it is the general goal of DCE-MRI processing algorithms to quantitatively study the local time dynamics of the tracer wash-in and wash-out processes for uncovering clues to the presence or absence of cancer or other abnormalities in the body part under study.

Because of the microscopic nature of vascular structures at the cellular scale, the individual compartments (plasma and EES) generally cannot be individually imaged because of voxel resolution limitations. Rather, for any particular voxel, only a value related (indirectly) to a total average tracer concentration $C_t(t)$ within that voxel is truly measurable. At any particular voxel, the relationship between the total average tracer concentration $C_t(t)$ (often simply termed the total tracer concentration), the plasma tracer concentration $C_p(t)$, and the EES tracer concentration $C_i(t)$ is provided by Eq. {1} below.

$$C_t(t) = v_p C_p(t) + v_i C_i(t) \quad \{1\}$$

In Eq. {1}, $v_p$ represents the percentage of total volume occupied by plasma, while $v_i$ represents the percentage of total volume occupied by EES.

In the context of DCE-MRI, local tissue physiology is often expressed in terms of one or more pharmacokinetic parameters that characterize one or more features of the tracer wash-in and wash-out process for that local tissue region. Examples of DCE-MRI pharmacokinetic parameters include a transfer constant $K^{trans}$, sometimes termed a permeability constant, and an extracellular volume parameter $v_e$, representing the percentage of all tissue volume lying outside the tissue cells ($v_e = v_p + v_i$), where tracer diffusion across the vessel walls is characterized by the first-order diffusion equation of Eq. {2} below.

$$\frac{dC_i(t)}{dt} = \frac{K^{trans}}{v_e}[C_p(t) - C_i(t)] \quad \{2\}$$

The relationship of Eq. {2} applies under a presumption that $v_i$, the percentage of total volume occupied by EES (often in the range of 10%-40%), is substantially greater than $v_p$, the percentage of total volume occupied by plasma (often in the range of 2%-3%), in which case the extracellular volume parameter $v_e$ substantially approximates $v_i$.

When viewed as a dynamical system with blood plasma tracer concentration $C_p(t)$ as the single input and extracellular tissue region $C_i(t)$ as the single output, the dynamical system defined by Eq. {2} is a first-order system with a time constant equal to $K^{trans}/v_e$ and an impulse response h(t) (the hypothetical value of $C_i(t)$ if the input $C_p(t)$ is assumed to be a unit impulse spike at time t=0) that is a decaying exponential, as illustrated in FIG. 1A. In a DCE-MRI PK parameter context, the time constant of the decaying exponential of FIG. 1A is often termed a rate constant $k_{ep}$, which is thus defined according to the relationship of Eq. {3}:

$$k_{ep} = \frac{K^{trans}}{v_e} \quad \{3\}$$

As is evident from Eq. {3}, determination of any two of the PK parameters $K^{trans}$, $v_e$, and $k_{ep}$ inherently determines the third. For the so-called "two-compartment" characterization of Eq. {2}, it is a goal of DCE-MRI processing to numerically determine, for each voxel, the PK parameters $K^{trans}$, $v_e$, and $k_{ep}$ by numerically processing a sequence of MRI volumes acquired at sequence of times subsequent to the injection of the tracer into the patient. One or more MRI volumes acquired prior to the tracer injection can also be used in conjunction with the post-injection MRI volumes. The inputs to the DCE-MRI processing algorithm are the set of MRI volumes and, for each MRI volume, the instant in time at which that MRI volume was acquired relative to the time of the tracer injection or other suitable reference time. The output of the DCE-MRI processing algorithm comprises three data volumes containing the values $K^{trans}$, $v_e$, and $k_{ep}$, respectively, for each voxel in the imaged volume.

FIGS. 1B and 1C conceptually illustrate one additional PK parameter $t_0$, termed a bolus arrival time difference. In particular, FIG. 1B illustrates a conceptual side view of a voxelwise map of tracer concentration values, a plasma reference region 106, and a typical voxel 108. It is often a key assumption for many DCE-MRI processing algorithms that the plasma concentration curve $C_p(t)$ is relatively uniform across the imaged tissue volume, and therefore that knowledge or estimation of the plasma concentration $C_p(t)$ at one location, such as a reference location 106, can also be used to represent the plasma concentration $C_p(t)$ at another location, such as at the voxel 108, during the computation algorithms that compute the PK parameters. Moreover, if particular reference regions 106 are known, based on their location in the anatomy, to have known "textbook" relationship estimates between their total tracer concentrations $C_t(t)$ and their plasma tracer concentrations $C_p(t)$ (e.g., the left ventricle, or the pectoral muscle, or the spleen), then the plasma concentration $C_p(t)$ can be estimated from the total concentration $C_{t,\,106}(t)$ at those locations, and then used volume-wide as an estimate of the plasma concentration $C_p(t)$ during computation of the PK parameters. The term plasma reference region is used herein to refer to such regions. The known "textbook" relationships are often provided in the form of the PK parameters themselves, which can be looked up for the left ventricle, pectoral muscle, spleen, etc., but which (of course) are valid only for those particular voxels in those locations.

However, there is often a delay between when the tracer material from a bolus tracer dose passes through the reference region 106 and when it passes through the voxel 108, which is termed the bolus arrival time difference $t_0$ for the voxel 108. As illustrated in FIG. 1C, this bolus arrival time difference $t_0$ can be readily incorporated into the impulse response h(t) for the voxel 108 and computationally uncovered by the PK computation algorithm along with the other PK parameters $K^{trans}$, $v_e$, and $k_{ep}$. Also, local variations in $t_0$ can be a further clue to the presence or absence of cancer or other abnormality at that locality.

From a practical perspective, the measurability of variations in $t_0$ with respect to the tissue anomalies that can be detected can serve as rough dividing lines between what is considered a slow MRI sequence and what is considered a fast MRI sequence. It has been found, for example, that there can be differences ($\Delta t_0$) in the bolus arrival time difference $t_0$ of about 4 seconds between malignant breast tissue and adjacent benign prostate tissue, and it is therefore desirable to acquire MRI sample volumes at a rate that is at least 4 seconds per sample volume in order to detect this difference. For the prostate, it has been found that there can be differences ($\Delta t_0$) in $t_0$ of about 1 second between malignant prostate tissue and adjacent benign prostate tissue and it is therefore desirable to acquire MRI sample volumes at a rate that is at least 1 second per sample volume in order to detect this difference. Rates slower than 4 seconds per sample for the breast and 1 second per sample for the prostate may thus serve as rough dividing lines between what is considered a slow MRI sequence versus a fast MRI sequence. Although one or more of the preferred embodiments hereinbelow is particularly advantageous for fast MRI sequences, it is to be appreciated that the scope of the preferred embodiments is not so limited and also extends to PK parameter computation for slow MRI sequences as well.

Many of the challenges in DCE-MRI arise because the voxel values of the data volumes actually received from the MRI system, which can be termed raw MRI volumes, unprocessed MRI volumes, or MRI reading volumes, are only indirectly related to the tracer concentration $C_t(t)$. FIG. 2 illustrates an approach to PK parameter computation according to a prior art method. At step 202, a time sequence of MRI reading volumes 203A-203E associated with a bolus tracer dose injection at a time $t_B$ is received. Another MRI volume 201 corresponding to a different MR sequence type acquired prior to the bolus tracer dose injection may also be received. The MRI volume 201 is generally in spatial registration with the MRI reading volumes 203A-203E, although their voxel resolutions might be different.

At step 204, a first tissue region useful for machine calibration is identified, usually in a manual manner by a radiologist. By way of example, the radiologist may manually circle (e.g., using a mouse) fat tissue on a slicewise display of the MRI volume 201 or, equivalently, one of the MRI reading volumes 203A-203E. At step 206, T1 values for the volume voxels are computed using the identified fat voxels of the first tissue region, a universally known T1 value for fat tissue (265 ms), and known MRI system parameters used during the volume acquisitions. The MRI volume 201 corresponding to the different MR sequence type may also be used at step 206. Then, at step 208, the T1 values are converted to total tracer concentration values $C_t(t)$ for each voxel. Accordingly, upon execution of step 208, there has been computed a volume 209 which, for each voxel, contains a time sequence of tracer concentration values for that voxel, as illustrated in FIG. 2.

At step 210, a second tissue region is identified that is a plasma reference region. Because the voxels of the second tissue region are identified as plasma reference regions, then their total tracer concentration $C_t(t)$, which was computed at step 208, can be used to compute the plasma tracer concentration $C_p(t)$ based on the known "textbook" values of $K^{trans}$, $k_{ep}$, and $t_0$. For each voxel, by virtue of the two-compartment model and Eq. {2}, the total tracer concentration $C_t(t)$ corresponds to a convolution of the plasma tracer concentration $C_p(t)$ with the impulse response h(t) of FIG. 1A or FIG. 1C. Generally speaking, known prior art methods use deconvolution-based approaches to compute $C_p(t)$ based on their knowledge of $C_t(t)$ and h(t), the latter being known (estimated) by virtue of "textbook" values of $K^{trans}$, $v_e$, $k_{ep}$, and $t_0$. Upon completion of step 210, there has been computed a time function $C_p(t)$ that can be used in computing the PK parameters in conjunction with the voxelwise $C_t(t)$ curves computed at step 208. Again in view of the two-compartment model and Eq. {2}, which dictates that $C_t(t)$ is the convolution $C_p(t)$ with h(t) at each voxel, at step 212 sample points for the function h(t) are computed for each voxel using a samplewise deconvolution of the total tracer concentration $C_t(t)$ computed at step 208 and the plasma tracer concentration $C_p(t)$ determined at step 210. Finally, at step 214, for each voxel, the PK parameters $K^{trans}$, $v_e$, $k_{ep}$, and $t_0$ are parametrically fitted to the sample points of h(t) that were computed at step 212.

One disadvantage of the method of FIG. 2 is that the deconvolution process is highly sensitive to noise and/or errors in the voxel data, which can reduce the accuracy of the results, introduce visual noise into visual maps of the parameters, or even become unstable and fail to converge altogether. Another disadvantage of the method of FIG. 2 relates to the identified plasma reference region used to estimate the plasma tracer concentration, the algorithm being sensitive to errors associated with the selection of the region or errors/noise in the raw voxel data. Still another disadvantage is that the deconvolution process is highly computationally intensive, requiring the use of more expensive hardware platforms.

The method of FIG. 2 also has disadvantages with respect to the practical usability of the system, especially when the often-preferable manual method is used for selection of the machine calibration reference tissue region (e.g., fat) and/or selection of the plasma reference tissue region. In particular, the highly computationally intensive deconvolution process needs to be performed after the reference tissue is identified.

Accordingly, there can be an undesirably long wait time between when the radiologist circles the reference region and when the final PK parameters are ready for display. This can be especially problematic if the radiologist wishes to interactively alter a reference tissue selection previously made, because the same long wait time needs to be endured after any change to the selection. It is to be appreciated that although particularly advantageous in conjunction with an interactive manual reference tissue identification process, the scope of the preferred embodiments described infra is not so limited.

More generally, other issues arise in the context of the DCE-MRI environment that are at least partially addressed by one or more of the preferred embodiments described herein. By way of example, the DCE-MRI process produces a large set of new data that, upon examination, may be indicative of an abnormal condition. Especially in view of the large amount of data already made available by the MRI medical imaging modality, new problems arise relating to increased workload, increased professional liability risk, decreased patient throughput, and increased per-patient cost.

Accordingly, it would be desirable to provide for more precise computation of PK parameters in a DCE-MRI environment in a manner that is more robust and stable against noise in the acquired MRI volumes and/or other input data errors.

It would be further desirable to provide such precise, robust, and stable computation of PK parameters in a manner that is faster, usable on less expensive hardware platforms, and more amenable to real-time, interactive user displays.

It would be still further desirable to provide an easy-to-use and easy-to-read interactive display for presenting PK parameters and/or other DCE-MRI related information.

It would be even further desirable to provide such PK parameter computation and/or interactive DCE-MRI-related display in a manner that is highly adaptable for, or otherwise applicable to, a variety of different body parts.

It would be still further desirable to compute and/or provide DCE-MRI-related data in a manner that addresses one or more of the workload, professional liability, and per-patient cost issues associated with the increased volume of data that is being made available. Other issues arise as would be apparent to one skilled in the art in view of the present disclosure.

SUMMARY

A system, computer program product, and related methods for processing and/or display of dynamic contrast-enhanced magnetic resonance imaging (DCE-MRI) information is provided. A plurality of instances of an MRI volume of the body part acquired at a respective plurality of sample times subsequent to an administration of a tracer is processed to determine a plurality of pharmacokinetic (PK) parameters characterizing a mathematical model-based relationship between a plasma tracer concentration and a total tracer concentration within the body part. For one preferred embodiment, computation of the PK parameters is performed according to a generalized signal model selected such that a first set of relatively intensive computations can be performed in non-real time prior to an interactive viewer session during which reference region identifications, required for PK computation, are input by the viewer. Advantageously, the generalized signal model is selected such that a second set of computations carried out subsequent to the viewer's reference region identifications are not intensive compared to the first set of computations, and can be promptly carried out in real time during the interactive viewer session. Accordingly, PK parameter computation can be carried out in real time during an interactive viewer session, the reference regions being selectable and optionally re-selectable by the viewer without requiring extensive waiting times for PK parameter computation.

According to another preferred embodiment, a fast PK parameter computation process is provided in which three or more plasma reference regions may be selected and incorporated into the PK parameter computation process to increase the accuracy thereof, while at the same time introducing a very minor amount of additional computation. Other advantages in PK parameter computation are also provided including accuracy and robustness against noise in the MRI volume data. In other preferred embodiments, associated user interfaces and computer-aided detection (CAD) algorithms are provided. In still other preferred embodiments, CAD algorithms are provided that leverage one or more of the preferred PK parameter computation embodiments in combination with magnetic resonance spectroscopy and/or tracer-enhanced magnetic resonance imaging information.

DETAILED DESCRIPTION

Figure 3:
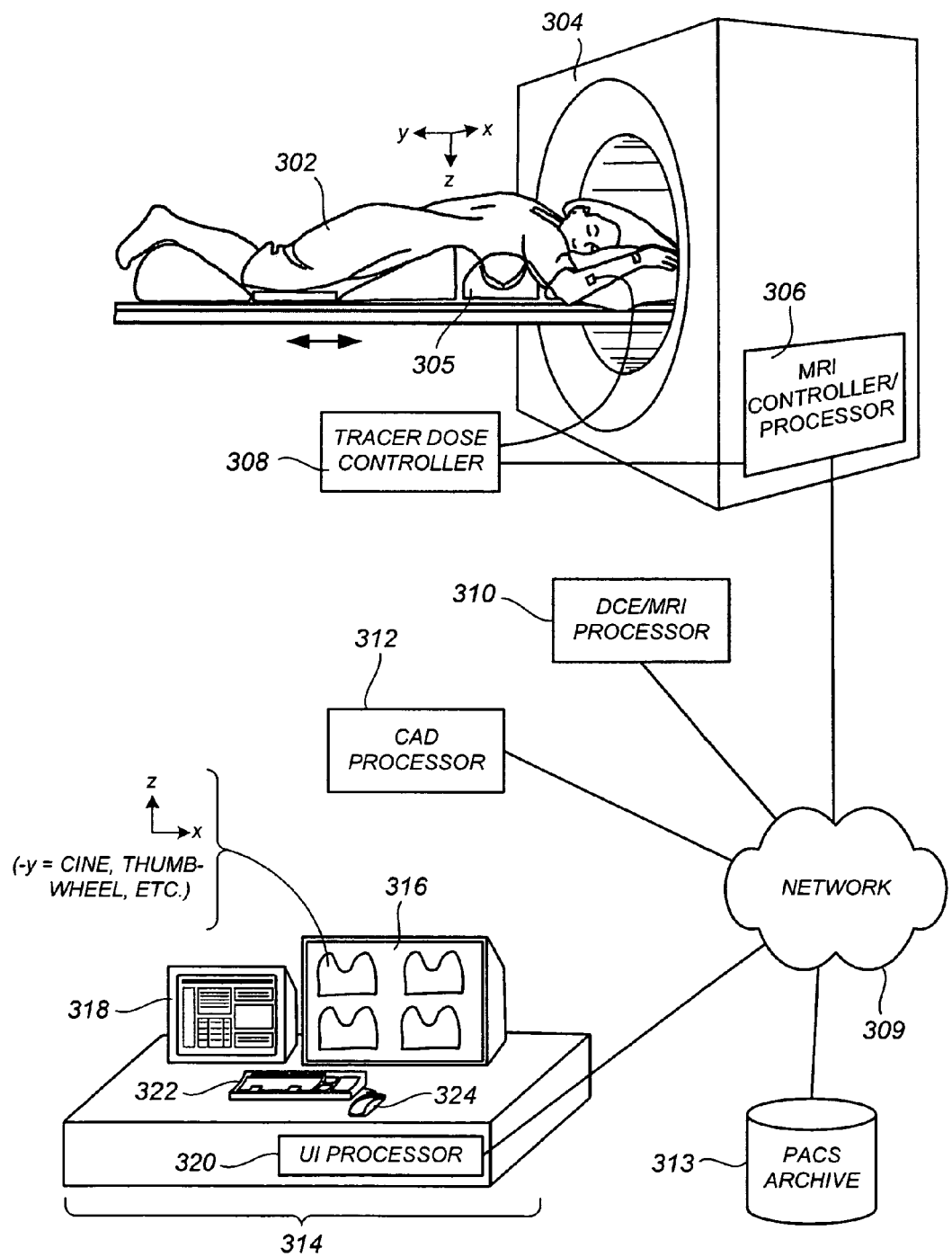
FIG. 3 illustrates a conceptual diagram of a medical imaging environment for which the processing and/or display of dynamic contrast-enhanced magnetic resonance imaging (DCE-MRI) information according to one or more of the preferred embodiments is particularly suitable.

FIG. 3 illustrates one example of a medical imaging environment for which the processing and/or display of dynamic contrast-enhanced magnetic resonance imaging (DCE-MRI) information according to one or more of the preferred embodiments is particularly suitable. The upper thorax of a patient 302 is imaged using an MRI system 304, the breasts of the patient being positioned in an MRI breast coil 305. Tracer material is intravenously introduced into the patient under the control of a tracer dose controller 308, which may be performed up to several times before and/or during the MRI imaging session. Several MRI volumes of the upper thorax are obtained under the control of an MRI controller/processor 306. As used herein, the several MRI volumes obtained by the MRI system 304 are termed raw MRI volumes for indicating that they represent "unprocessed" inputs to the DCE-MRI and/or CAD system algorithms described further infra. Although many of the raw MRI images provided by the MRI system 304 are T1-weighted images in one or more of the embodiments infra, the term raw MRI images as used herein is not necessarily limited to T1-weighted images.

The medical imaging environment further comprises a network 309, which may be a HIS/RIS (Hospital Information System/Radiology Information System) network, to which is coupled the MRI controller/processor 306, as well as a DCE-MRI processor 310 and a computer-aided detection (CAD) processor 312. The DCE-MRI processor 310 receives the raw MRI volumes from the MRI controller/processor 306 and performs some or all of the pharmacokinetic (PK) parameter computations described further herein. The CAD processor 312 receives the results (intermediate and/or final) generated by the DCE-MRI processor 310, and/or one or more of the raw MRI volumes from the MRI controller/processor 306, and processes them to automatically detect anatomical abnormalities in the breast or other body part being imaged.

Also coupled to the network 309 is a PACS (Picture Archiving and Communication System) archive 313, generally representing a repository for medical information associated with the medical imaging environment, including both current and archived images, current and archived CAD results, radiology reports for completed cases, and so forth. Preferably, the various medical images and related information are communicated according to the DICOM (Digital Imaging and Communications in Medicine) standard and the network 309 supports the TCP/IP protocol, which is used as the transport protocol for the DICOM standard.

Also coupled to the network 309 is a review workstation 314, which may be a dedicated MRI review workstation, a dedicated DCE-MRI/CAD workstation, or a generic multi-modality workstation having plug-ins for providing the processing and displaying functionalities described herein and/or ports for otherwise accessing these functionalities. Review workstation 314 comprises a diagnostic monitor 316, an administrative monitor 318, a keyboard 322 and mouse 324 or other user input devices (e.g., trackball, pointers, etc), and a user interface processor 320. Administrative monitor 318 is used for input and output of a wide variety of information that may be associated with a particular set of medical images (e.g., listings, tables, plots, text descriptions, etc), as well as for system installation, maintenance, updating, and related tasks. Generally speaking, the administrative monitor 318 can be a relatively low-cost monitor as would be found in generic information processing environments. However, the diagnostic monitor 316 should be FDA-approved as having sufficient luminance, contrast, resolution, and other characteristics that qualify it as proper medical image screening and/or diagnosis tool.

For one or more preferred embodiments, the DCE-MRI processor 310 and CAD processor 312 collectively perform their computations and generate their results in an entirely automated manner, optionally including the user interface processor 320 for automated display processing, without requiring any user input. For other preferred embodiments, at least one of the DCE-MRI processing, CAD processing, and display processing require interactive user input from a radiologist or other medical professional viewing one or more of the raw or processed MRI images at the review workstation 314. As used herein, radiologist generically refers to a medical professional that analyzes medical images and makes clinical determinations therefrom, it being understood that such person might be titled differently, or might have differing qualifications, depending on the country or locality of their particular medical environment.

Notably, the medical imaging environment of FIG. 3 is presented by way of example only and is not intended to limit the scope of the preferred embodiments to this particular scenario, this particular set of hardware, or this particular body part. For example, DCE-MRI information processing and/or display according to one or more of the preferred embodiments can be advantageously applied for body parts other than the breast, such as the prostate. Different combinations of the hardware devices of FIG. 3, such as the tracer dose controller 308, the CAD processor 312, and the user interface processor 320 can be placed adjacently to each other or integrated into the same hardware without departing from the scope of the preferred embodiments. By way of still further example, the network 309 can be a wide-area network with the different elements illustrated in FIG. 3 being distributed throughout a city, a country, or the world. Alternatively, and by way of still further example, some or all of the transfer of digital information among devices can be achieved by physical transfer of disks, memory sticks, or other digital media devices without departing from the scope of the preferred embodiments. The processing of DCE-MRI information according to one or more of the preferred embodiments can be performed on any of a variety of different hardware platforms, using any of a variety of different workflow/business models (e.g., using remotely connected radiologists, off-site ASP-provided information processing, etc.) without departing from the scope of the preferred embodiments. In view of the present disclosure, a person skilled in the art would be able to construct the processing/display algorithms, plug-ins, or other software packages capable of achieving the described processing and/or user interface functionalities without undue experimentation using publicly available or otherwise known programming tools and software development platforms.

Figures 1, 4:
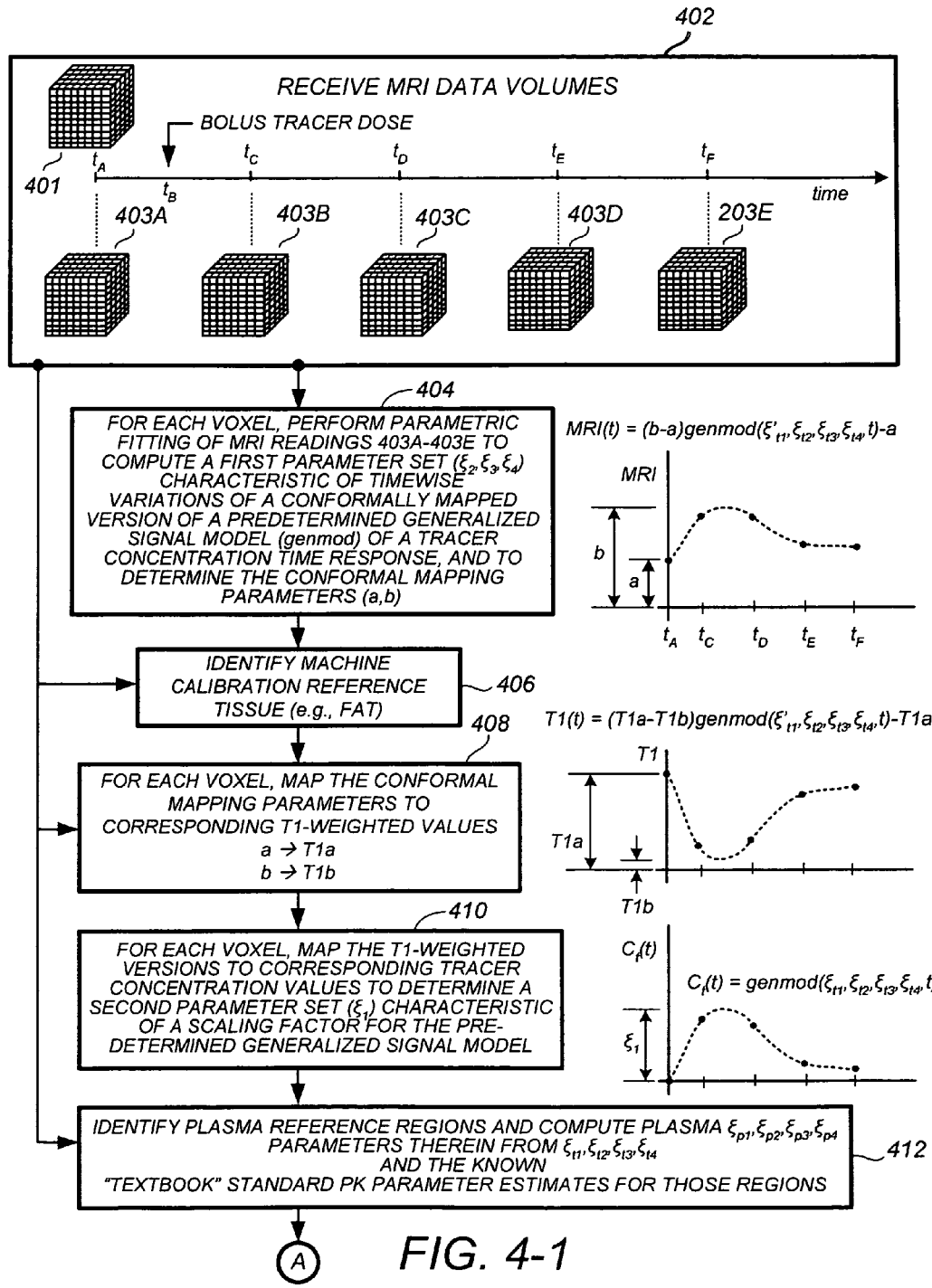
FIG. 4 illustrates a method for PK parameter computation according to a preferred embodiment.
Figures 2, 4:
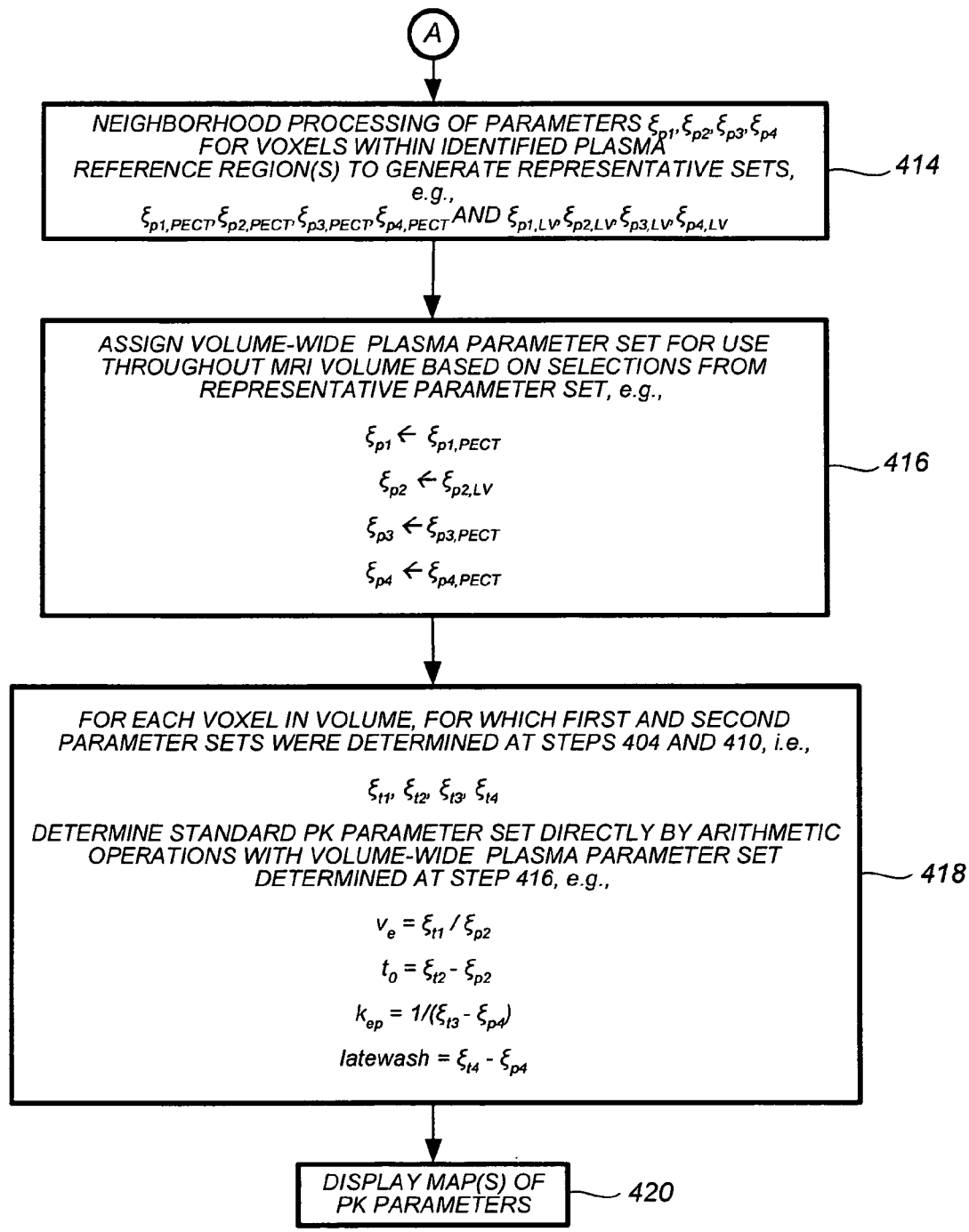

FIG. 4 illustrates a method for PK parameter computation according to a preferred embodiment. At step 402, a time sequence of MRI reading volumes 403A-403E associated with a bolus tracer dose injection at a time $t_B$ is received. Another MRI volume 401 corresponding to a different MR sequence type acquired prior to the bolus tracer dose injection may also be received. By way of example, the MRI reading volumes 403A-403E may be acquired under a first MR sequence such as a dynamic T1-weighted acquisition protocol, while the MRI volume 401 may by acquired under a second MR sequence such as a proton density protocol. The MRI volume 401 is generally in spatial registration with the MRI reading volumes 403A-403E, although their voxel resolutions might be different.

At step 404, for each voxel, a parametric fitting of the MRI readings 403A-403E is performed to compute a first parameter set ($\xi_2$, $\xi_3$, $\xi_4$) characteristic of timewise variations of a conformally mapped version of a predetermined generalized signal model genmod($\xi_1,\xi_2,\xi_3,\xi_4$,t) of a tracer concentration time response, and to determine the conformal mapping parameters. Preferably, the generalized signal model genmod ($\xi_1,\xi_2,\xi_3,\xi_4$,t) is selected such that (i) it will resemble a form of a total tracer concentration curve $C_t(t)$ for at least some parameter values, (ii) it will resemble a form of a plasma tracer concentration curve $C_p(t)$ for at least some parameter values, (iii) it is separable between a first subset of parameters (for example, the parameters $\xi_2,\xi_3$, and $\xi_4$) that are determinative of its timewise variations and a second subset of parameters (for example, the parameter $\xi_1$) that are determinative of its scale, and (iv) the desired standard PK parameters are related to the generalized signal model parameters according to relatively simple mathematical relationships, such as straightforward arithmetic relationships comprising addition, multiplication, subtraction, or division. One such generalized signal model, expressed in termed of a Laplace domain representation, is illustrated in Eq. (4) below.

$$gen\text{mod}(s|\xi) = C(s|\xi) = \xi_1 \frac{e^{-\xi_2 s}}{s}\left(\frac{1}{1+\xi_3 s}\right)(1+\xi_4/s^2) \quad \{4\}$$

Generally speaking, $\xi_1$ is determinative of a peak/plateau concentration, $\xi_2$ is representative of the bolus arrival time, $\xi_3$ is representative of a time-to-peak, and a late part of the curve after the wash-in phase is at least partially characterized by a slope $\xi_4$, termed herein latewash. Eqs. (5)-(6) below restate the generalized signal model of Eq. (4) for each of the total tracer concentration $C_t$ and the plasma tracer concentration $C_p$.

$$C_t(s) = \xi_{t1}\frac{e^{-\xi_{t2}s}}{s}\left(\frac{1}{1+\xi_{t3}s}\right)(1+\xi_{t4}/s^2) \quad \{5\}$$

$$C_p(s) = \xi_{p1}\frac{e^{-\xi_{p2}s}}{s}\left(\frac{1}{1+\xi_{p3}s}\right)(1+\xi_{p4}/s^2) \quad \{6\}$$

As can be seen upon inspection of the form of Eqs. (5)-(6), the parameters $\xi_2, \xi_3$, and $\xi_4$ characterize timewise variations of the tracer concentrations $C_t(t)$ and $C_p(t)$, but not an overall scale. In contrast, the parameter $\xi_1$ is determinative of a scale of the tracer concentrations $C_t(t)$ and $C_p(t)$, but not the timewise variations. Referring again to FIG. 4, and particularly to the conceptual plots of voxel tracer concentration "C(t)" adjacent to block 410 and raw voxel reading "MRI" adjacent to block 404, one or more of the preferred embodiments takes advantage of a general observation, determined generally valid, that the timewise features of the actual voxel tracer concentration "C(t)" will end up having the same basic timewise variations as the raw voxel readings "MRI", except for a scaling and a translation (i.e., a "conformal mapping" as that term is applied to scalar functions of a single variable). Thus, if a parameter set $\xi_2, \xi_3$, and $\xi_4$ is computed that characterizes timewise variations of "MRI", then that same parameter set also characterizes the timewise variations (but not the scale) of voxel tracer concentration "C(t)". Accordingly, once the parameters $\xi_2, \xi_3$, and $\xi_4$ have been computed for any particular sequence of raw MRI volumes, they will not need to be computed again, regardless of any subsequent activity relating to machine calibration (i.e., mapping between the raw MRI readings and a relaxation time metric such as T1) and/or patient calibration (i.e., "removal" of plasma tracer concentration from each voxel to determine the PK parameters from the measured total tracer concentration at that voxel). Stated equivalently, once the parameters $\xi_2, \xi_3$, and $\xi_4$ have been computed for any particular sequence of raw MRI volumes, they will not need to be computed again, even after the fat voxel identification and plasma reference voxel identification has been made and/or changed.

Referring still to step 404, also computed thereat are conformal mapping parameters "a" and "b" that correspond to a shifting and scaling of the "MRI" curve. Without loss of generality, the parameter "a" usually corresponds to a "static" value of the MRI curve prior to the introduction of the bolus tracer dose, while the parameter "b" usually corresponds to a "peak" or "plateau" of the "MRI" curve that is achieved prior to the washing out of the tracer material. The particular magnitudes of the shifting and scaling are generally meaningless until machine calibration is achieved, at which time these values are used to determine the scaling factor $\xi_1$. Generally speaking, in accordance with a preferred embodiment, the "heavy" computations (more particularly, the parametric fitting algorithms) associated with the particular sequence of raw MRI volumes are completed as of step 404, and the computations for the remaining steps of the method of FIG. 4 are relatively light and quick in comparison thereto.

At step 406, a first tissue region useful for machine calibration (e.g., fat) is identified, usually in a manual manner by a radiologist, or alternatively is automatically identified by an automated segmentation algorithm. At step 408, the conformal mapping values "a" (static) and "b" (peak/plateau) are mapped into corresponding T1 values (or other suitable relaxation time metric values), shown as T1a and T1b in FIG. 4, using the identified fat voxels of the first tissue region, a universally known T1 value for fat tissue (265 ms), and known MRI system parameters used during the MRI volume acquisitions. The MRI volume 401 corresponding to the different MR sequence type is also used at step 408. Known methods can be used to carry out the machine calibration at steps 406-408. In other preferred embodiments, multiple reference regions, and not just fat regions, can be used for the machine calibration. For example, two or more regions of two or more tissue types can be selected for machine calibration provided that their T1 values are universally known or can otherwise be estimated.

At step 410, the values for T1a (T1-static) and T1b (T1-peak/plateau) are mapped into total tracer concentration values to an extent sufficient to determine the scaling factor $\xi_1$. Usually, the scaling factor $\xi_1$ will simply be the total tracer concentration value corresponding to T1b (T1-peak/plateau), because the total tracer concentration value corresponding to T1a (T1-static) would, of course, need to be zero or close to zero.

Thus, at the end of step 410, there has been computed, for each voxel of the imaged volume, a complete set of parameters ($\xi_{t1}, \xi_{t2}, \xi_{t3}, \xi_{t4}$) characterizing the total tracer concentration curve $C_t(t)$ according to Eq. {5}, supra. What remains in the algorithm is to determine the standardized PK parameters $K^{trans}$, $v_e$, $k_{ep}$, and $t_0$. At step 412, at least one tissue region, and preferably two or more tissue regions, are identified that are known to be plasma reference, also by manual identification or automated segmentation. Examples include the left ventricle and the pectoral muscle for breast DCE-MRI, and spleen for prostate DCE-MRI. Because the voxels therein are identified as plasma reference, then their known total tracer concentration parameters ($\xi_{t1}, \xi_{t2}, \xi_{t3}, \xi_{t4}$) can be used as a basis for a volume-wide estimate of the plasma tracer concentration parameters ($\xi_{p1}, \xi_{p2}, \xi_{p3}, \xi_{p4}$), again under the key assumption that, except for the bolus arrival time difference $t_0$, the plasma concentration is relatively uniform across the imaged tissue volume.

For one preferred embodiment, at step 414, any of a variety of neighborhood-based processing of the total tracer concentration parameters ($\xi_{t1}, \xi_{t2}, \xi_{t3}, \xi_{t4}$) can be performed across the identified regions such that a "best" or "representative" parameter set serves as the basis for the tracer concentration parameters for that region. Thus, shown in FIG. 4 at step 414 are a best plasma tracer concentration parameter set (($\xi_{p1,PECT}, \xi_{p2,PECT}, \xi_{p3,PECT}, \xi_{p4,PECT}$) for the pectoral muscle, and a best plasma tracer concentration parameter set ($\xi_{p1,LV}, \xi_{p2,LV}, \xi_{p3,LV}, \xi_{p4,LV}$) for the left ventricle. Advantageously, this neighborhood processing serves to make the algorithm more accurate and robust against noise or other errors associated with the plasma tissue identification. At step 416, selected ones of the "best" plasma tracer concentration parameter sets are chosen to represent a final optimal plasma tracer concentration parameter set ($\xi_{p1}, \xi_{p2}, \xi_{p3}, \xi_{p4}$) to be used as the estimated plasma tracer concentration across the entire volume. In another preferred embodiment, only the particular parameters to be assigned in step 416 need to be neighborhood-processed in their respective regions at step 414, that is, ($\xi_{1,PECT}, \xi_{2,PECT}, \xi_{3,LV}, \xi_{4,PECT}$) for the example of FIG. 4. This selection of three parameters from the pectoral muscle and one from the left ventricle is usually predetermined according to empirical observation of best algorithm performance, but optionally can be user-selectable. Advantageously, multiple different reference tissues can be selected, and their associated parameters can be selected, combined, or otherwise processed to generate a single, reliable, volume-wide plasma tracer concentration parameter set ($\xi_{p1}, \xi_{p2}, \xi_{p3}, \xi_{p4}$). For one preferred embodiment, three different plasma reference regions are identified and used. For another preferred embodiment, four different plasma reference regions are identified and used. For yet another preferred embodiment, five or six different plasma reference regions are identified and used.

At step 418, the final volume-wide plasma tracer concentration parameter set ($\xi_{p1}, \xi_{p2}, \xi_{p3}, \xi_{p4}$) determined at step 416 is processed, for each voxel in the volume, in conjunction with the local total tracer concentration parameter set ($\xi_{t1}, \xi_{t2}, \xi_{t3}, \xi_{t4}$) determined at steps 404 and 410, to determine the desired standardized PK parameters $K^{trans}$, $v_e$, $k_{ep}$, and $t_0$. The computations of step 418, which advantageously consist of simple, direct arithmetic computations (e.g., addition, subtraction, multiplication, division) using the parameters sets ($\xi_{p1}, \xi_{p2}, \xi_{p3}, \xi_{p4}$) and ($\xi_{t1}, \xi_{t2}, \xi_{t3}, \xi_{t4}$), can be better understood with respect to Eqs. (7)-(10) below.

Figure 1A:
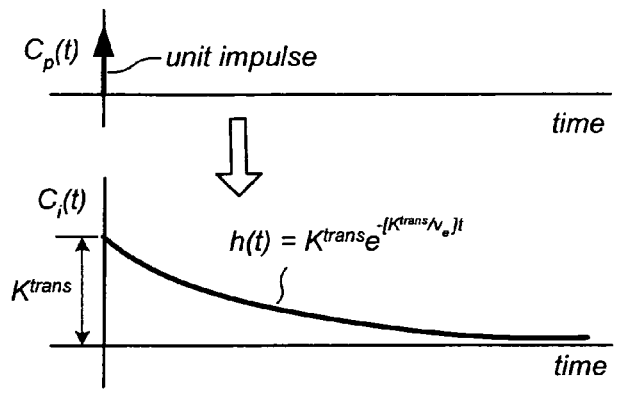
FIG. 1A illustrates an impulse response associated with a pharmacokinetic (PK) model.
Figure 1B:
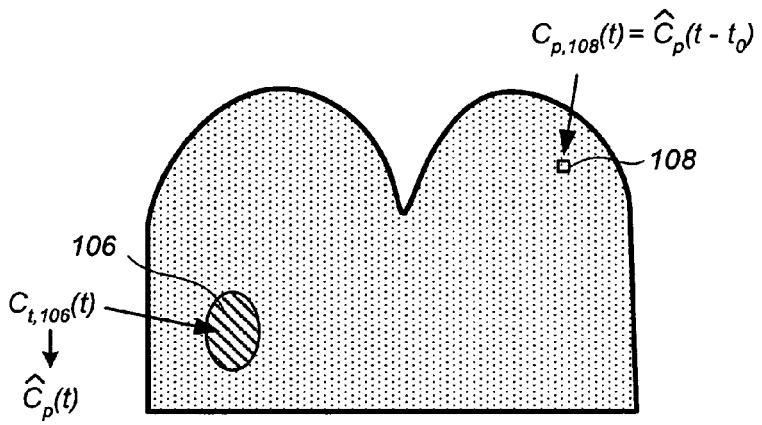
FIG. 1B illustrates a conceptual side view of a voxelwise map of tracer concentration values.
Figure 1C:
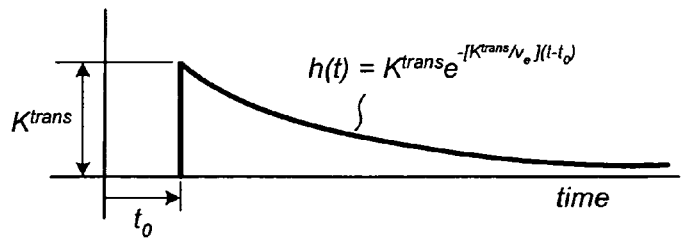
FIG. 1C illustrates an impulse response associated with a pharmacokinetic (PK) model.

Eq. (7) below represents an approximation of a result of the Laplace domain division $C_t(s)/C_p(s)$ as each appears in Eqs. (5) and (6), supra, this Laplace domain division corresponding to a Laplace transform of the impulse response h(t) of a dynamical system having $C_p$ as the input and $C_t$ as the output. The Laplace transform of this impulse response h(t) is termed the tissue transfer function H(s). The particular form of H(s) shown in Eq. (7), which is an outcome of the selection of the generalized signal model of Eq. (4), is particularly advantageous in light of the standardized two-compartment PK parameter model impulse response h(t) illustrated in FIG. 1C, the Laplace transform of which is illustrated in Eq. (8).

$$H(s) = \frac{C_t(s)}{C_p(s)} \quad \{7\}$$

$$\approx \frac{\xi_{t1}}{\xi_{p1}} e^{(\xi_{t2}-\xi_{p2})s} \left(\frac{1}{1+(\xi_{t3}-\xi_{p3})s}\right)(1+(\xi_{t4}-\xi_{p4})/s^2)$$

$$H(s) = K^{trans} e^{t_0 s}\left(\frac{1}{(K^{trans}/v_e)+s}\right) \quad \{8\}$$

$$= v_e e^{t_0 s}\left(\frac{1}{1+(1/k_{ep})s}\right)$$

Comparing Eq. (7) to Eq. (8), it is readily seen that there is a direct arithmetic correspondence between the generalized signal model parameters $\xi_{p1}, \xi_{p2}, \xi_{p3}, \xi_{p4}, \xi_{t1}, \xi_{t2}, \xi_{t3}, \xi_{t4}$ and the standardized PK parameters $K^{trans}$, $v_e$, $k_{ep}$, and $t_0$ according to the relationships of Eqs. (9)-(11) below. These relationships are set forth under a presumption, determined valid, that the partial expression at the right end of Eq. (7) relating to the latewash factors does not practically alter the correspondence that is otherwise observable between the parameter sets. Indeed, according to a preferred embodiment, a latewash parameter "latewash" as expressed in Eq. (12) below is added to the standard PK parameter set and serves as an additional clue to anomalous tissue conditions.

$$v_e = \xi_{t1}/\xi_{p1} \quad \{9\}$$

$$t_0 = \xi_{t2} - \xi_{p2} \quad \{10\}$$

$$k_{ep} = 1/(\xi_{t3} - \xi_{p3}) \quad \{11\}$$

$$latewash = \xi_{t4} - \xi_{p4} \quad \{12\}$$

$$k_{ep} = \frac{K^{trans}}{v_e} \quad \{3\}$$

Finally, at step 420, a map of the computed PK parameters is provided on a user display for viewing by a radiologist, preferably as an overlay to a display of the MRI volume 401, or a different high-resolution MRI image volume acquired before or after the dynamic sequence of MRI readings 403A-403E.

Figure 2:
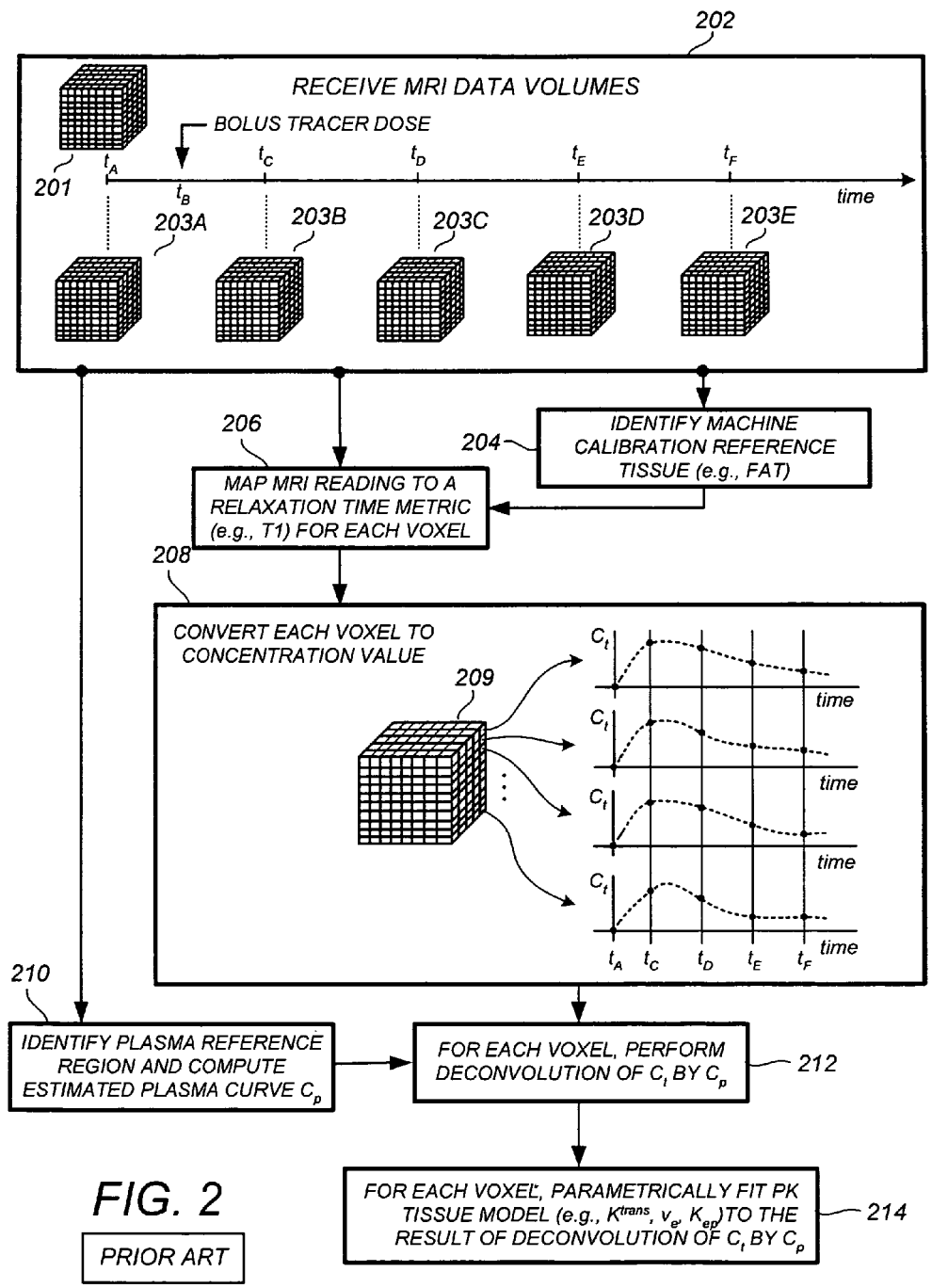
FIG. 2 illustrates a deconvolution-based PK parameter computation method.

For one preferred embodiment, the step 404 is carried out in non-real time, during a delay between the actual MRI acquisition process and the viewing of the resultant data by the radiologist. This delay can often be anywhere between 30 minutes and several days, and often corresponds to a "natural" delay associated with clinical workflow processes, and not an unwanted computational delay. Then, during the interactive viewing session, the radiologist manually selects the reference tissue areas for machine calibration (fat) or patient calibration (plasma). When computed according to the preferred embodiment of FIG. 4, there can be an almost instantaneous display of the PK parameters responsive to the manual selection, because the computation steps subsequent to the curve-fitting step 404 are often quickly performed even by hardware that is low-powered by medical imaging standards. In addition to enjoying the prompt initial display, the radiologist can interactively re-select the reference tissue areas and almost immediately see the resultant changes in the computed PK parameters. These advantages are additional to other advantages of accuracy, stability, and robustness as compared to the PK computation algorithm of FIG. 2, supra.

With reference again to FIG. 4, supra, according to one of more of the preferred embodiments, the PK parameter computation process is functionally divided between (i) a time-intensive pre-computation process that does not require reference region identification, and (ii) a relatively light computational process subsequent to reference region identification. This enables a rich set of inventive user interface features to be provided, because the waiting time between reference region identification and provision of PK parameters is substantially diminished. The "absolute" clinical relevance of the PK parameter overlays is also increased, because the computed values are more consistent across different patients and different MRI acquisition systems. Thus, for example, with respect to a color-coded $K^{trans}$ overlay, corresponding tissue regions for two different patients having the same color and brightness are now more likely to actually correspond to similar tissue conditions.

Also enabled by the generalized model-based PK parameter computation process described above, which from at least one perspective can be loosely termed a "Laplacian method", are a rich set of inventive computer-aided detection and/or diagnosis (CAD) algorithms, whether fully manually interactive, partially automated, or fully automated, by virtue of the increased reliability and reduced noise in the computed PK parameters. The availability of more reliable and reduced-noise PK parameters is particularly advantageous in a CAD classifier training context, because the PK parameters will be more consistent across different patients, which results in a higher quality classifier training data set.

Figure 5:
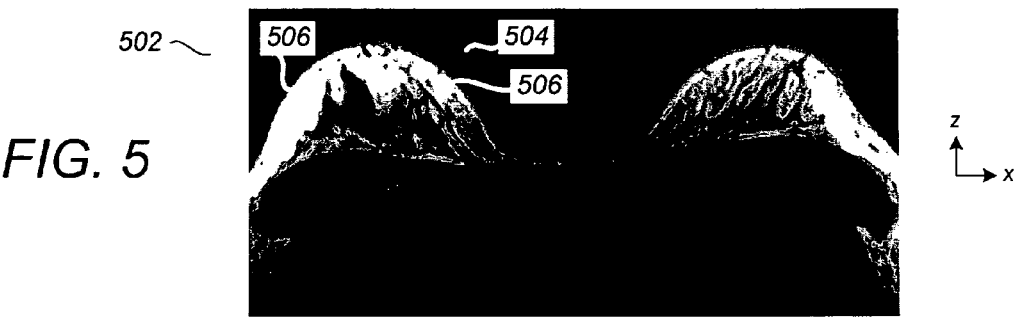
FIG. 5 illustrates a display of a grayscale viewable MRI image that may be the basis for receiving user identifications of machine calibration regions and/or plasma reference regions according to a preferred embodiment.

FIG. 5 illustrates a display of a grayscale viewable MRI image 502 that may be the basis for receiving user identifications of machine calibration regions and/or plasma reference regions according to a preferred embodiment. As used herein, viewable MRI volume refers to an MRI volume associated with the dynamically imaged sequence of MRI volumes 403A-403E (for example, acquired during the same patient MRI session with the patient in the same position) that can be viewed by a physician on the review workstation, as well as various combinations thereof of processing results produced therefrom. Examples of viewable MRI volumes include T1-weighted volumes (which can be one of the MRI reading volumes 403A to 403E, T1 volumes (i.e., post-machine-calibration versions of T1-weighted volumes), difference volumes, and other MRI volume types. Where the MRI reading volumes 403A-403E are dynamic T1-weighted volumes, one particularly useful viewable volume is a difference volume comprising a voxelwise difference between a post-contrast T1-weighted volume (e.g., one of the volumes 403B-403E) and the pre-contrast T1-weighted volume 403A. Other difference volumes formed from the MRI reading volumes (e.g., 403E minus 403B), as well as between T1 versions of the MRI reading volumes, can also be useful. As used herein, a viewable volume can be at the same voxel resolution or a different voxel resolution as the raw MRI readings 403A-404E. For example, if a very fast sequence is acquired, thereby needing a relatively low resolution compared to slower sequences, a higher resolution version of the breast can be acquired during the same patient session, which can then serve as the viewable volume.

For the particular example of FIG. 5, the viewable MRI volume 502 is a high resolution T1-weighted volume, acquired during a relatively slow dynamic sequence that was acquired during the same patient imaging session as a relatively fast dynamic sequence. Although the fast sequence can achieve better timewise resolution for the PK parameter estimation, the slower sequence often contains images that are better candidates for the viewable images. By way of example only, and not by way of limitation, the for a 3.0 T magnetic field in the MRI machine, the slow sequence may have been acquired at 90-second intervals and may have a resolution of 384×192×160 voxels sized at 0.88 mm×0.88 mm×1 mm, whereas the fast sequence may have been acquired at 4-second intervals and have a resolution of 128×52×64 voxels sized at 2.65 mm×2.65 mm×2.5 mm. Appearing as white in FIG. 5 on a breast 504 are fat regions 506.

Figure 6:
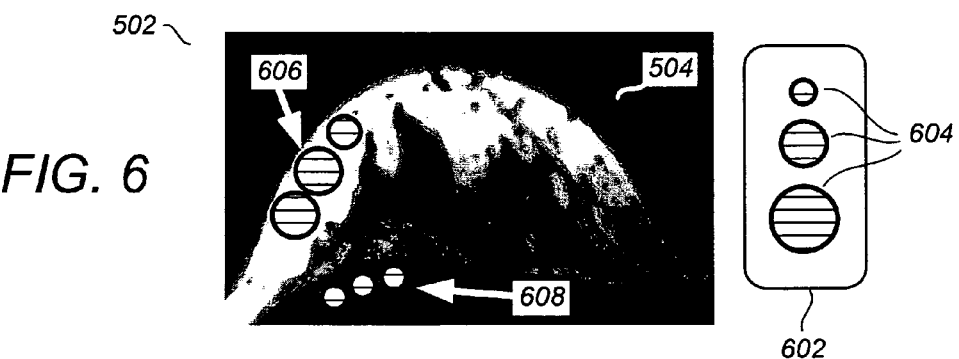
FIG. 6 illustrates a user interface for identifying machine calibration regions and/or plasma reference regions according to a preferred embodiment.

FIG. 6 illustrates a user interface for identifying machine calibration regions and/or plasma reference regions according to a preferred embodiment. A menu 602 containing differently-sized region markers 604 is provided such that the user can click-and-drag the region markers over the displayed viewable image to delineate the desired reference regions. Other input (not shown) can be provided to delineate between fat reference locations 606 and pectoral muscle locations 608, or other types of reference tissue. Optionally, the base set of region markers can be re-sized manually by the viewer. The actual tissue that is selected responsive to the clicking and dragging is three-dimensional as shown in FIG. 7.

Figure 7:
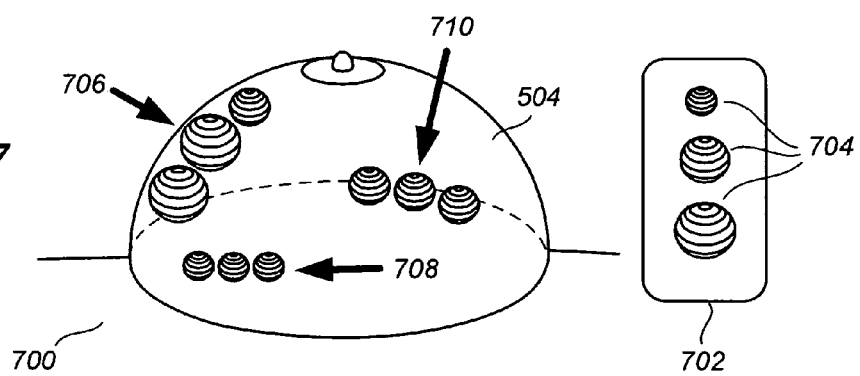
FIG. 7 illustrates a user interface for identifying machine calibration regions and/or plasma reference regions according to a preferred embodiment.

FIG. 7 illustrates a user interface for identifying machine calibration regions and/or plasma reference regions according to a preferred embodiment, which is analogous to the preferred embodiment of FIG. 6, supra, except that the breast 504 is shown in a three-dimensional view (such as a maximum intensity projection image or other 3D image display method), and a menu 702 of volumetric reference markers 704 is provided. In addition to the volumetric markers 706 and 708 corresponding to the region markers 606 and 608, respectively, FIG. 7 also shows other volumetric markers 710 placed "out-of-plane" relative to the other markers, which is made more convenient by the interface of FIG. 7. Advantageously, many different shapes can be "built" by dragging together many different 2D and/or 3D markers, so that just the right desired reference region can be easily drawn and used even if it has relatively complex contours.

Figure 8A:
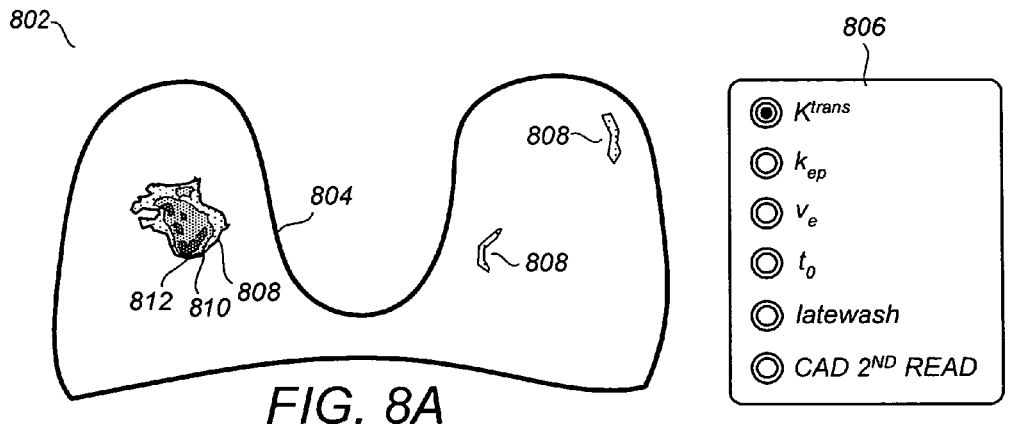
FIGS. 8A-8B illustrates a DCE-MRI user interface with PK parameter overlay display according to a preferred embodiment.
Figure 8B:
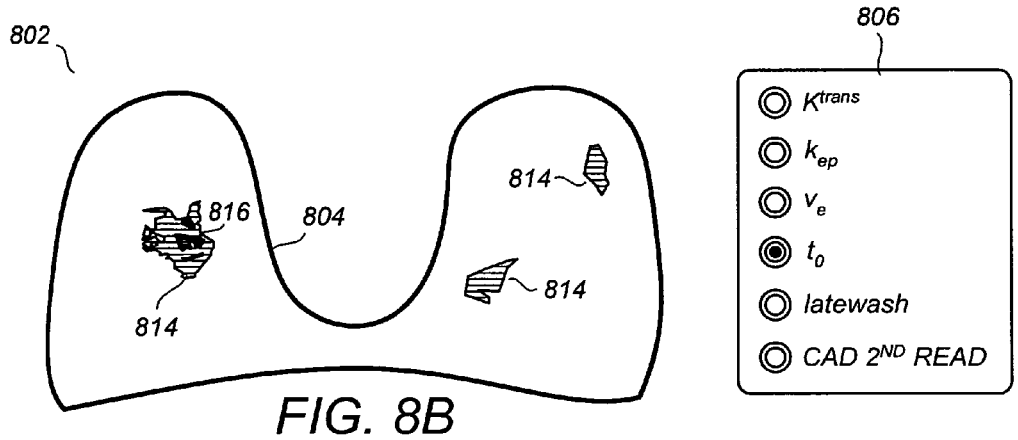

FIGS. 8A-8B illustrate a DCE-MRI user interface 802 with PK parameter overlay display upon a viewable volume 804 according to a preferred embodiment. A menu 806 with radio buttons (for example) is provided to allow selective display of the different PK parameters, which appear color-coded on the display. For the $K^{trans}$ example of FIG. 8A, three different $K^{trans}$ magnitude levels 808, 810, and 812 appear, In FIG. 8B, two different time ranges 814 and 816 are graphically represented for the bolus arrival time different $t_0$, although it is to be appreciated that many more levels for each resembling a color continuum for each can be used.

Figure 8C:
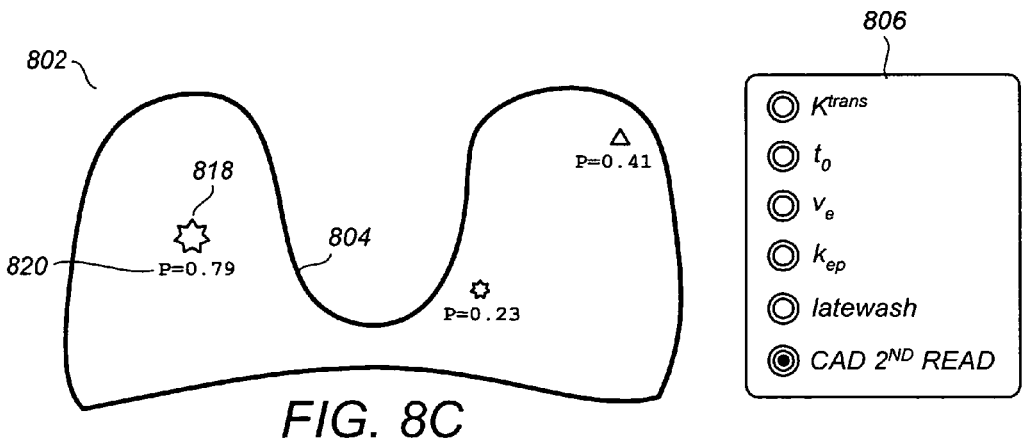
FIG. 8C illustrates a DCE-MRI CAD output display according to a preferred embodiment.

FIG. 8C illustrates a DCE-MRI CAD output display 802 according to a preferred embodiment. Overlaid upon the viewable volume 804 is an annotation map showing CAD finding markers 818, next to which malignancy probability levels 820 are shown.

Figure 9:
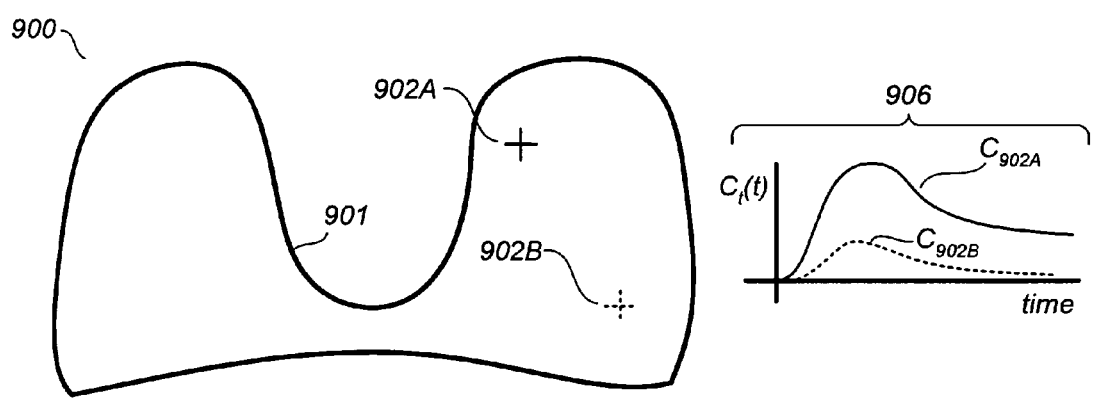
FIG. 9 illustrates a DCE-MRI user interface with selective user-controlled display of per-voxel tracer concentration wash-in and wash-out curves according to a preferred embodiment.

FIG. 9 illustrates a DCE-MRI user interface display 900 according to a preferred embodiment. When the user clicks on a particular location 902A on a viewable volume image 901, a time plot $C_{902A}$ is displayed showing the total tracer concentration at that voxel. When the user clicks on a different location 902B, the time plot changes to a new corresponding plot $C_{902B}$.

Figure 10:
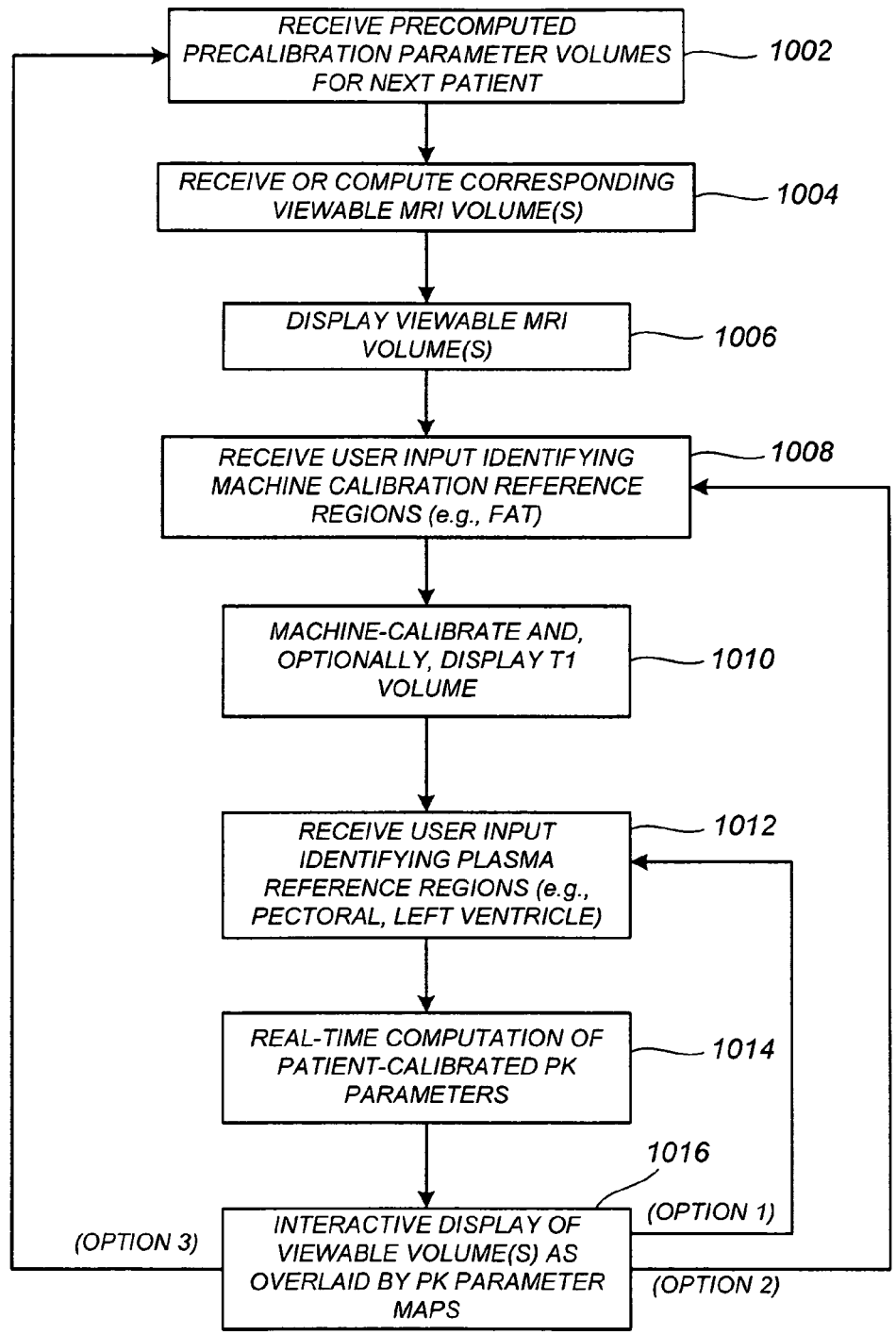
FIG. 10 illustrates a method for interactive DCE-MRI PK parameter computation and display according to a preferred embodiment.

FIG. 10 illustrates a method for interactive DCE-MRI PK parameter computation and display according to a preferred embodiment. At step 1002 a set pf precalibration parameter volumes are received for the next patient., the precalibration parameter volumes ($\xi'_{t1}, \xi_{t2}, \xi_{t3}, \xi_{t4}$) corresponding to the results of step 404 of FIG. 4, which represented the more difficult, time-intensive computations, but which did not require any viewer input and so could be performed in non-real time prior to the interactive session. At step 1004 the corresponding viewable MRI volumes are received and then displayed at step 1006. At step 1008 the viewer (e.g., radiologist) identifies the machine calibration reference regions (see FIGS. 6-7), and at step 1010 the machine calibration computations are performed (see FIG. 4, steps 406-408). The calibrated T1 volume can optionally be displayed. At step 1012 the plasma reference regions are manually identified by the viewer (also see FIGS. 6-7), followed by quick, fast, real-time PK parameter computation at step 1014 as enabled by the preferred embodiments supra. The PK parameter images are then interactively and selectively overlaid upon the viewable MRI volumes as described above with respect to FIGS. 8-9.

Figure 11:
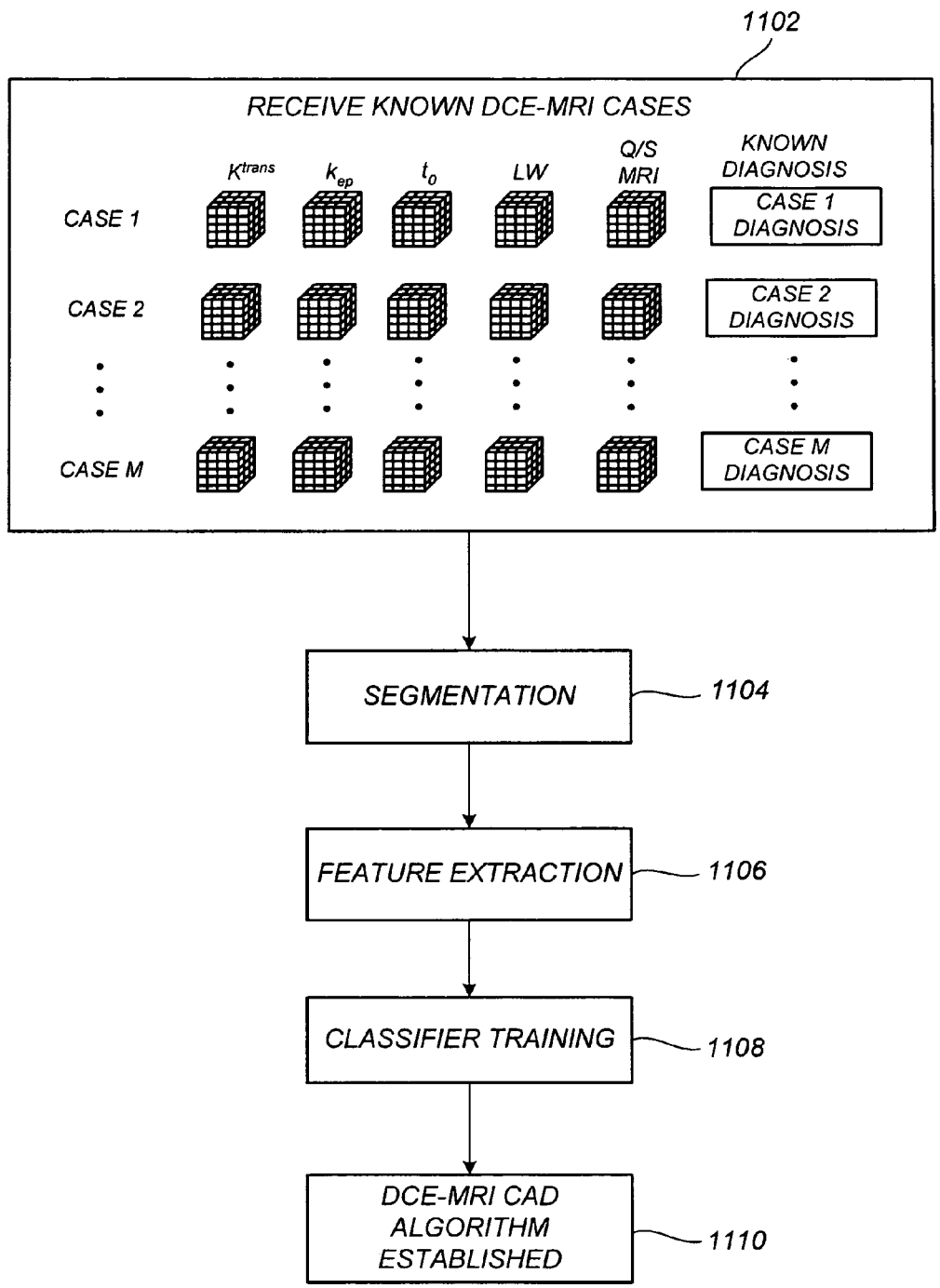
FIG. 11 illustrates DCE-MRI CAD algorithm training according to a preferred embodiment.

FIG. 11 illustrates DCE-MRI CAD algorithm training according to a preferred embodiment. At step 1102, a large collection of breast (or prostate) DCE-MRI cases having known diagnoses is received, including a sufficient number (preferably in the hundreds or thousands). It is preferable that the PK parameter computation process of FIG. 4 was used to compute PK parameter sets. Alternative to receiving the PK parameter sets, the raw set of MRI volumes acquired at the successive time intervals (not shown) for each case can be received, and the PK parameters computed as part of step 1102. As still another alternative, both the raw set of MRI volumes and the PK parameter sets can be received. Preferably, included in the DCE-MRI volume data for each case is at least one useful static or quantitative MRI volume, such as a T1 volume, a proton density volume, a T2 volume, a T2* volume, or other type of MRI volume from which tissue structure may be segmented or otherwise identified, which is represented in FIG. 11 as a "Q/S MRI" volume (quantitative and/or static). The Q/S MRI volumes can also include one or more viewable volume described above with respect to FIG. 10.

At steps 1104-1106, three-dimensional segmentation is performed and three-dimensional geometric and/or statistical features are extracted for each of the viewable volumes. Examples of three-dimensional geometric features of the segmented shapes include, but are not limited to, mass size, mass border roughness or smoothness, spiculatedness, sphericity/eccentricity, surface area-to-volume, and so forth. Examples of three-dimensional statistical features include heterogeneity metrics, maximum/minimum values, median values, average values, etc., on a volume-wide or subvolume-wide basis, as measured within or around a segmented geometrical shape, including the use of voxel values from the PK parameter volume sets.

At step 1108, the three-dimensional geometric and/or statistical features are used to train a classifier algorithm. The classifier algorithm may incorporate any of a variety of classification algorithms known in the art, including linear classifier algorithms, quadratic classifier algorithms, K-nearest-neighbor classifier algorithms, decision tree classifier algorithms, or neural network classifier algorithms. At step 1110, the established algorithm is stored on a computing platform for subsequent clinical use to detect and/or diagnose tissue abnormalities for unknown cases.

Figure 12:
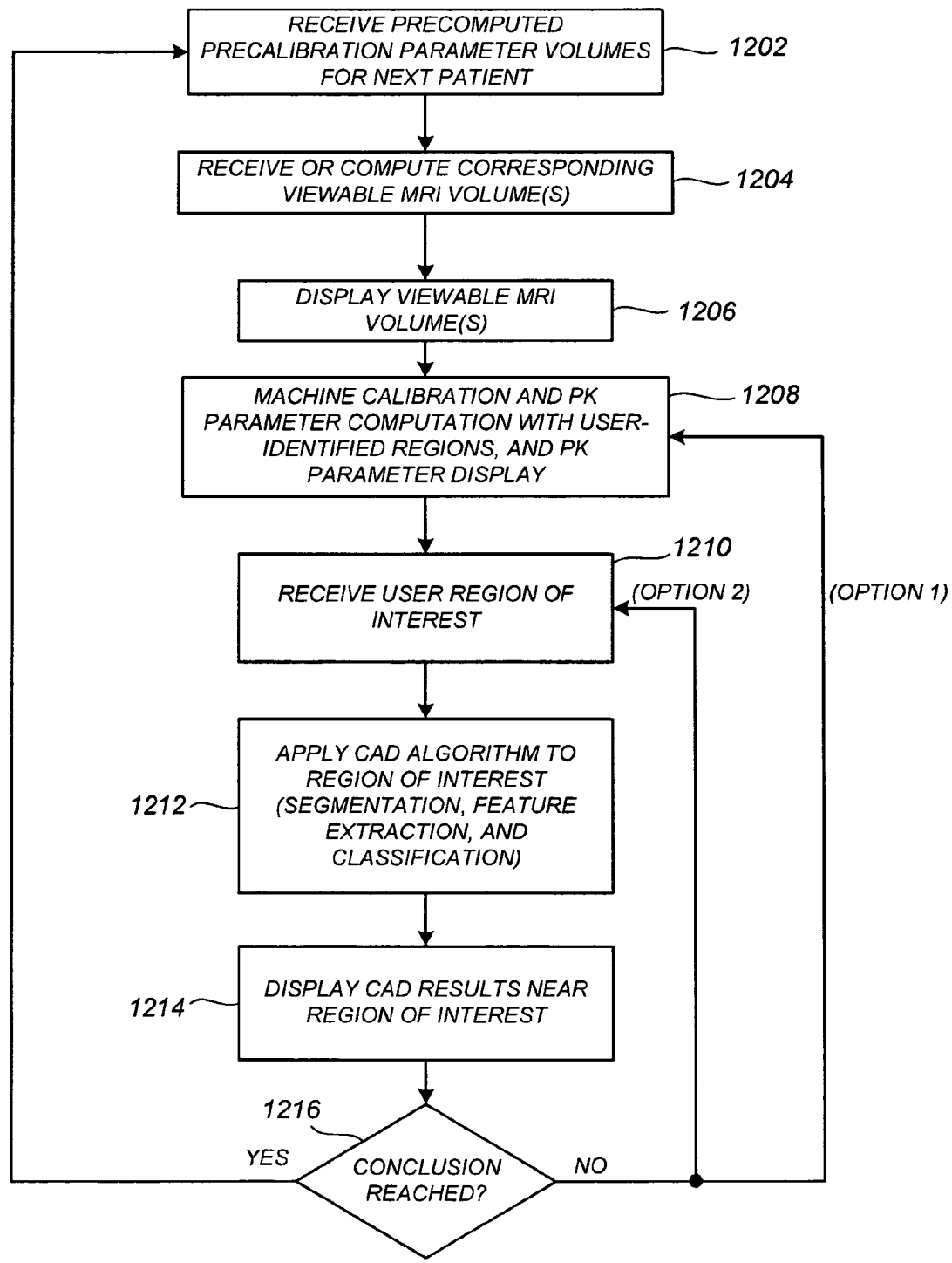
FIG. 12 illustrates a user interfacing method for a DCE-MRI data review workstation according to a preferred embodiment.
Figure 13:
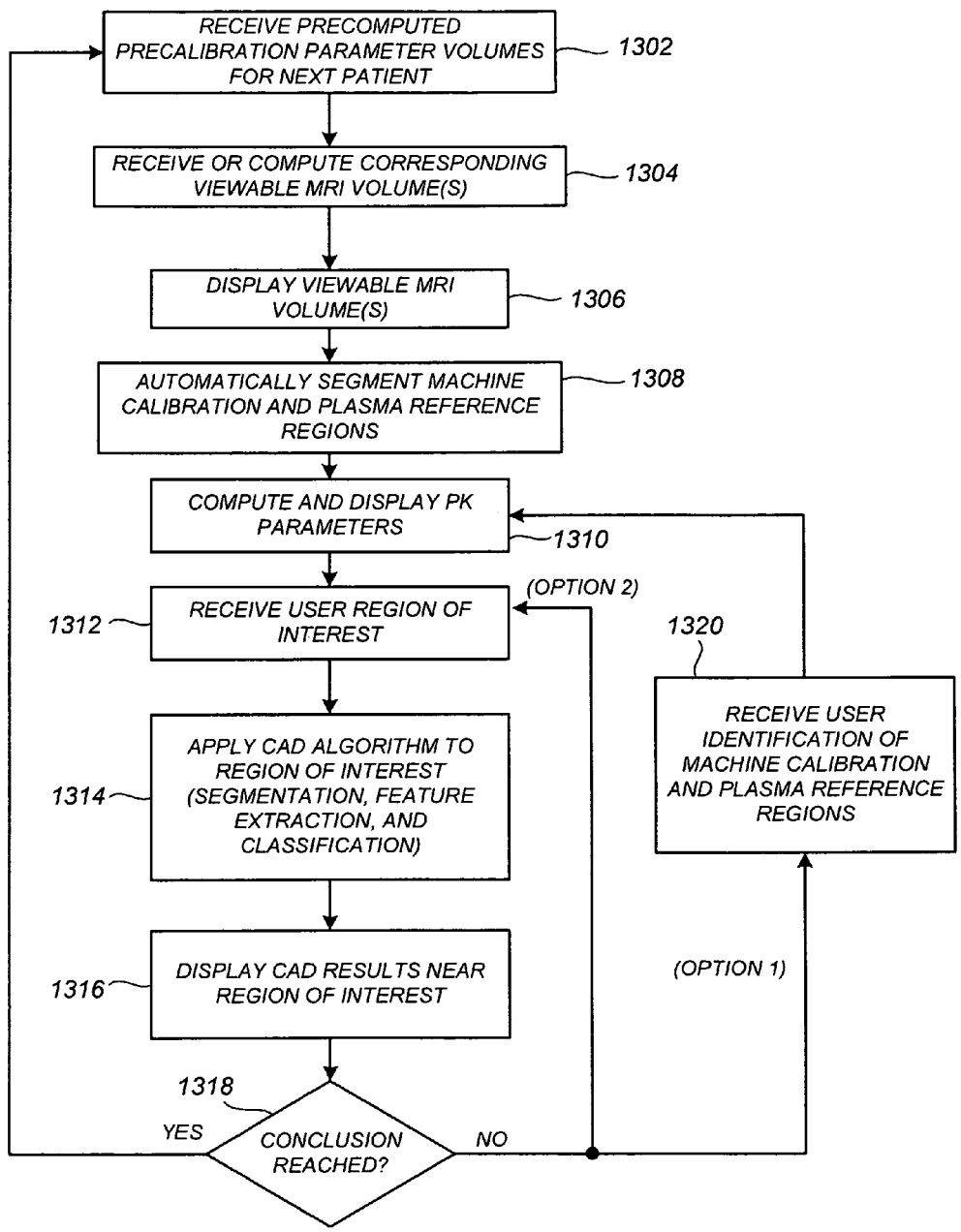
FIG. 13 illustrates a user interfacing method for a DCE-MRI data review workstation according to a preferred embodiment.

FIG. 12 illustrates a user interfacing method for a DCE-MRI data review workstation according to a preferred embodiment. Here, the machine calibration and plasma reference regions are manually identified by the user (step 1208) and regions of interest for CAD analysis are also manually identified (step 1210) by the user. FIG. 13 illustrates a user interfacing method for a DCE-MRI data review workstation according to a preferred embodiment in which machine calibration and plasma reference regions are automatically computer segmented prior to the interactive user session using known methods (step 1308), but can be manually altered by the user (step 1320) if desired for recomputation of PK parameters. Also in the preferred embodiment of FIG. 13, the regions of interest for CAD analysis are manually identified by the user (step 1314).

Figure 14:
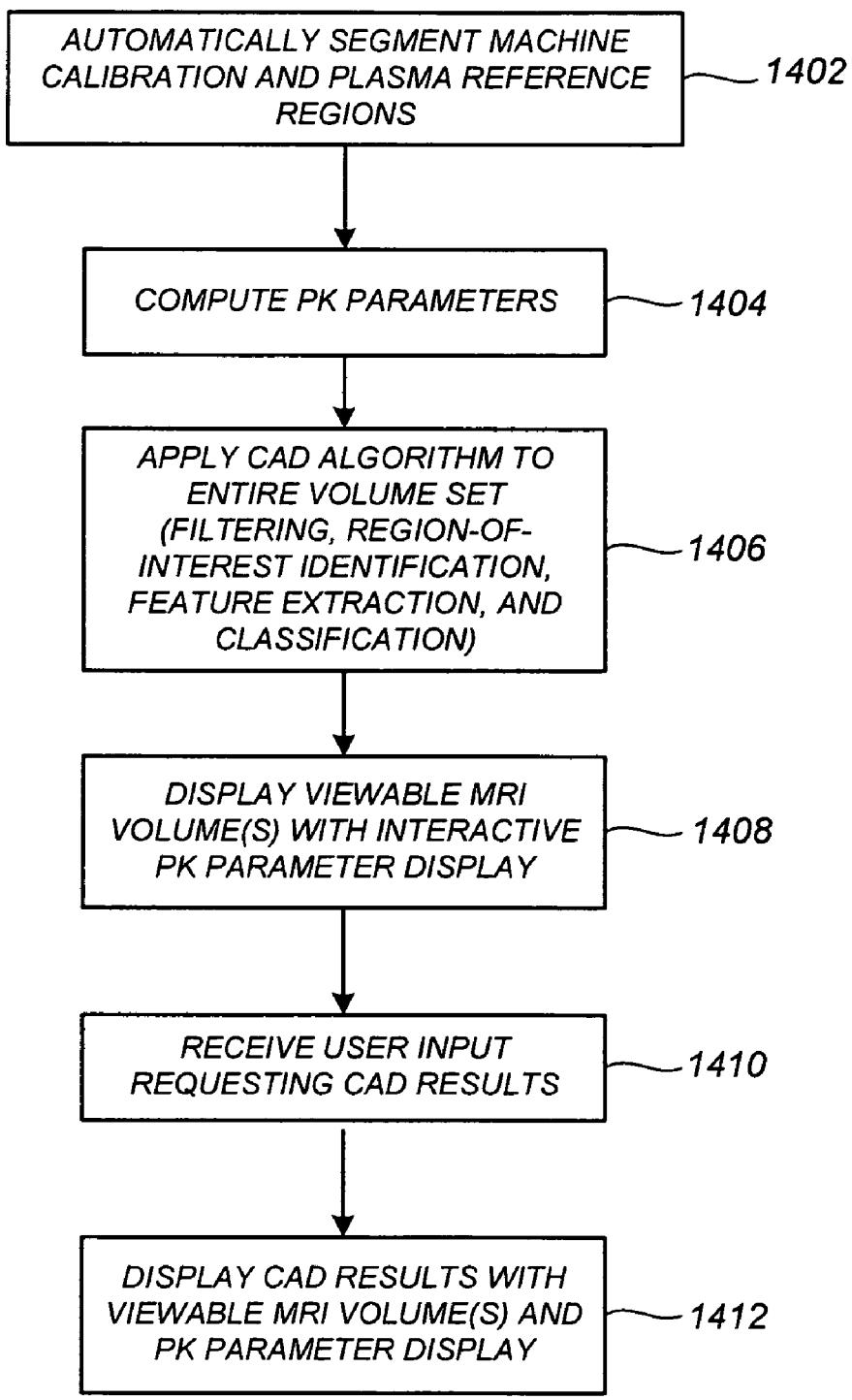
FIG. 14 illustrates a user interfacing method for a DCE-MRI data review workstation according to a preferred embodiment.

FIG. 14 illustrates a user interfacing method for a DCE-MRI data review workstation according to a preferred embodiment in which machine calibration (step 1402), patient calibration and PK parameter computation (step 1404), and CAD identification and classification of suspicious locations (1406) are performed automatically, without requiring any input from the user. An annotated map (see FIG. 8C) can be provided (step 1412) along with the PK parameter overlays upon receipt of a CAD request from the viewer.

Figure 15:
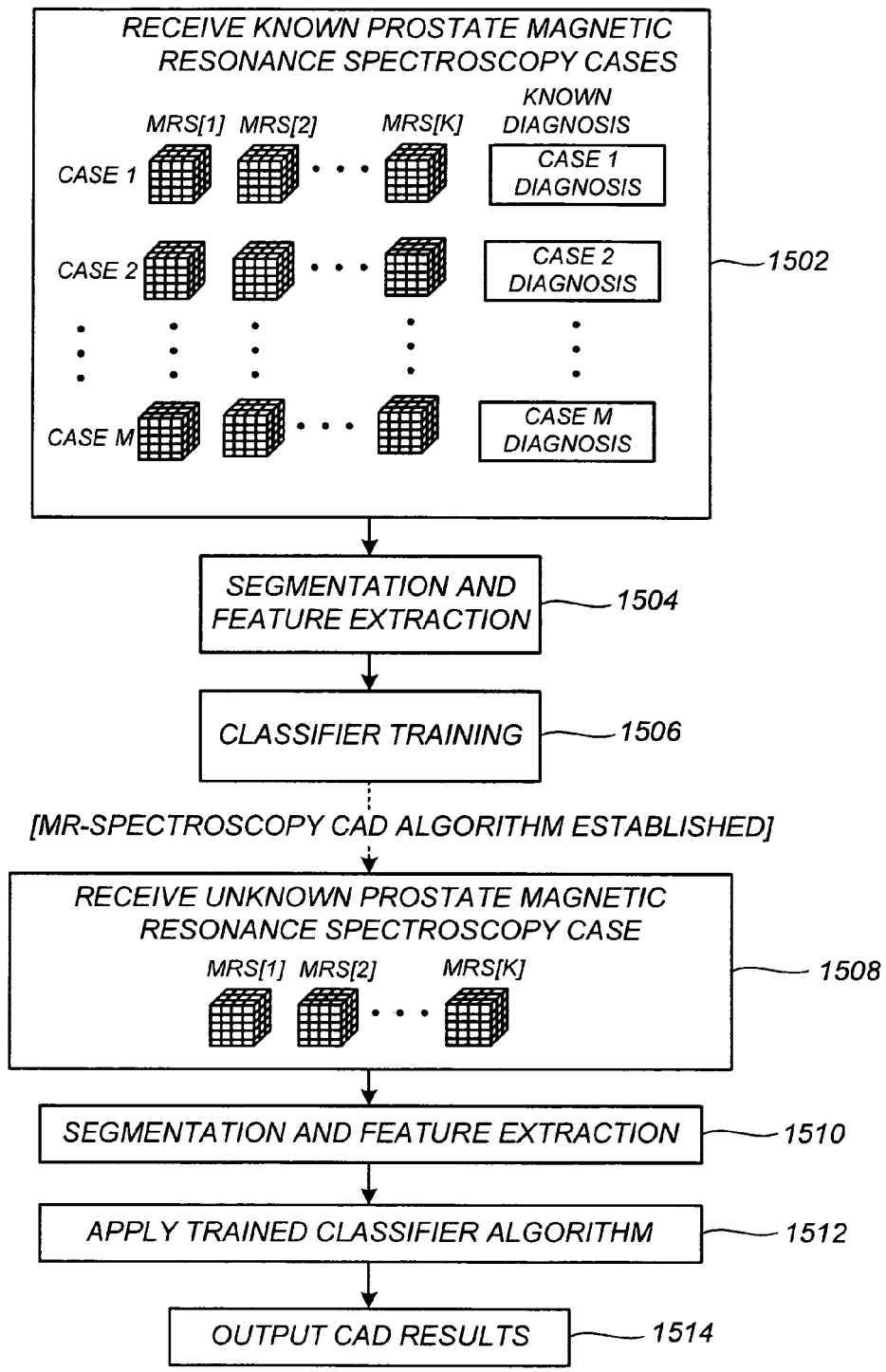
FIG. 15 illustrates computer-aided detection and/or diagnosis (CAD) for magnetic resonance spectroscopy according to a preferred embodiment.

FIG. 15 illustrates computer-aided detection and/or diagnosis (CAD) for magnetic resonance spectroscopy according to a preferred embodiment. According to a preferred embodiment, three-dimensional volumes comprising magnetic resonance spectroscopy (MRS) information on a per-voxel basis for the prostate are processed for automatic detection and/or diagnosis of tissue abnormalities, such as cancer, in the prostate. This process is referred to herein as MRS CAD for the prostate, or prostate MRS CAD. According to another preferred embodiment, three-dimensional volumes comprising MRS information on a per-voxel basis for the breast or other body organ are processed for automatic detection and/or diagnosis of tissue abnormalities therein, such as cancer (i.e., breast MRS CAD or other-organ MRS CAD. Without loss of generality, a particular preferred embodiment for prostate MRS CAD is described hereinbelow.

Magnetic resonance spectroscopy (MRS) combines the spatially-addressable nature of MRI with spectroscopic information obtainable from nuclear magnetic resonance (NMR) imaging. In MRS, a magnetic nuclear isotope (such as proton, deuterium, tritium, carbon 13, fluorine 19, sodium 23, or phosphorus 31) absorbs radio frequency energy when placed in a magnetic field. This energy absorption causes a resonance of the nuclei of the atoms in the chemical compound being examined. Because different atoms resonate at different frequencies, the resonance frequency reveals structural information about the chemical compound. When used for medical imaging, the MRS imaging process yields, for each voxel, a 1-dimensional (or higher) NMR frequency spectrum having spectral peaks corresponding to the presence of particular atoms or molecules. Of particular interest are certain metabolite molecules, such as choline, citrate, creatine, lipid, and lysine, whose quantities and/or ratios may be clinically associated with the presence of cancerous tumors. Thus, for example, cancerous prostate tissue has been found to have a high choline/citrate ratio, whereas healthy prostate tissue maintains a low choline/citrate ratio.

Three-dimensional MRS volumes MRS[k] processed by a preferred prostate MRS CAD algorithm each comprise a data value associated with one or more outputs of the MRS process. By way of example, MRS[1] may comprise a ratio of spectral peak intensities for choline to citrate for each voxel, MRS[2] may comprise the spectral peak intensity for lysine, MRS[3] may comprise the spectral peak intensity for choline, and so forth.

Prostate MRS CAD according to a preferred embodiment generally comprises training of a prostate MRS CAD algorithm using known cases, followed by clinical use of the prostate MRS CAD algorithm by application to unknown cases. At step 1502, the volumes MRS[k] associated with a sufficient population of MRS-imaged prostates with known diagnoses, including a sufficient number of malignant diagnoses, are received.

At step 1504, three-dimensional geometric and/or statistical features are extracted from each of the volumes MRS[k] and/or from various other volumes comprising voxelwise functions of the volumes MRS[k]. The three-dimensional geometric feature comprise numerical descriptors of three-dimensional shapes (if any) resulting from the application of one or more segmentation algorithms to the voxel data. Because the volumes being segmented can themselves represent fairly abstracted quantities (e.g., choline/citrate signal intensity ratios), the segmented shapes (if any) might not resemble familiar anatomical shapes. However, there may be certain patterns in this abstracted data found to be highly associated with anomalous tissue conditions, and these can be automatically detected by the present prostate MRS CAD algorithm when configured and trained according to the preferred embodiments. Examples of three-dimensional geometric features of the potentially-segmented shapes include, but are not limited to, mass size, mass border roughness or smoothness, spiculatedness, sphericity/eccentricity, surface area-to-volume, and so forth. Examples of three-dimensional statistical features include heterogeneity metrics, maximum/minimum values, median values, average values, percentile values, etc., on a volume-wide or subvolume-wide basis, or as measured within or around a segmented geometrical shape.

At step 1506, the three-dimensional geometric and/or statistical features are used to train a classifier algorithm. The classifier algorithm may incorporate any of a variety of classification algorithms known in the art, including linear classifier algorithms, quadratic classifier algorithms, K-nearest-neighbor classifier algorithms, decision tree classifier algorithms, or neural network classifier algorithms. The trained algorithm is then stored on a computing platform for subsequent clinical use to detect and/or diagnose tissue abnormalities for unknown cases.

At step 1508, a set of three-dimensional MRS volumes MRS[k] corresponding to a prostate of a patient of a medical clinic are received. At step 1210, three-dimensional geometric and/or statistical features are extracted using methods similar to those of step 1504. At step 1512, the extracted features are processed by the classifier algorithm that was previously trained at step 1206. Finally, at step 1512, an output is provided that identifies suspicious locations and a probability of malignancy for each of the suspicious locations. This can be provided in the form of an annotated road map of the suspicious lesions interactively overlaid upon, and in spatial registration with, a medical image of the prostate acquired from any of the volumes MRS[k] or acquired from another imaging modality, such as a tracer-enhanced T1-weighted MRI image of the prostate. Alternatively to steps 1508-1512, an interactive CAD user interface can be used in which regions of interest are first identified and/or segmented by the radiologist and then CAD-processed in real time.

Figure 16:
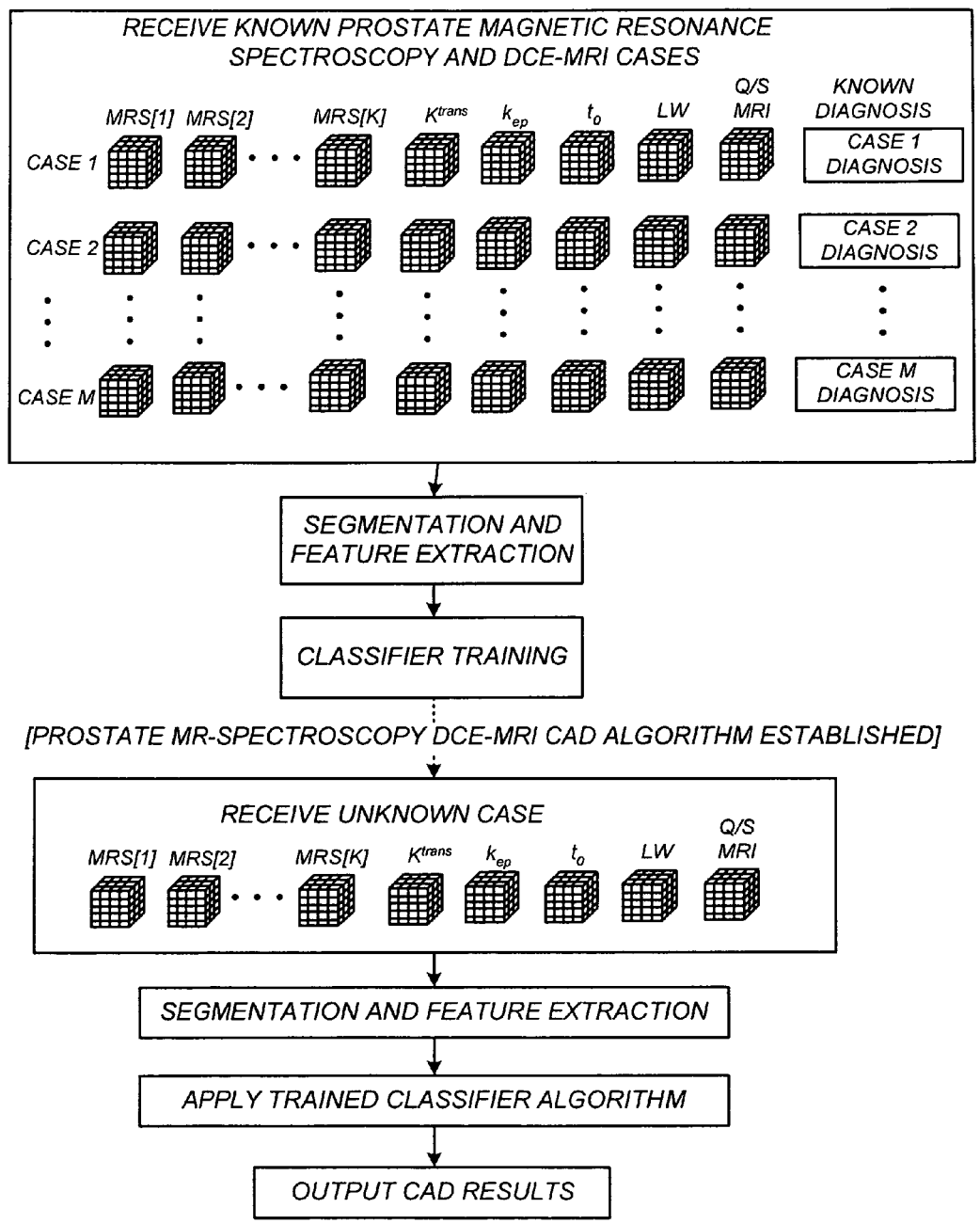
FIG. 16 illustrates combined CAD using magnetic resonance spectroscopy and DCE-MRI PK parameter information according to a preferred embodiment.

FIG. 16 illustrates computer-aided detection and/or diagnosis (CAD) for the prostate according to a preferred embodiment, wherein both magnetic resonance spectroscopy (MRS) and DCE-MRI PK parameter information is processed, termed herein prostate MRS/DCE-MRI CAD. As illustrated in FIG. 16, training and clinical use of the preferred prostate MRS/DCE-MRI algorithm proceeds in a manner analogous to the preferred embodiment of FIG. 15, except that both MRS[k] and DCE-MRI volume data are used.

Figure 17:
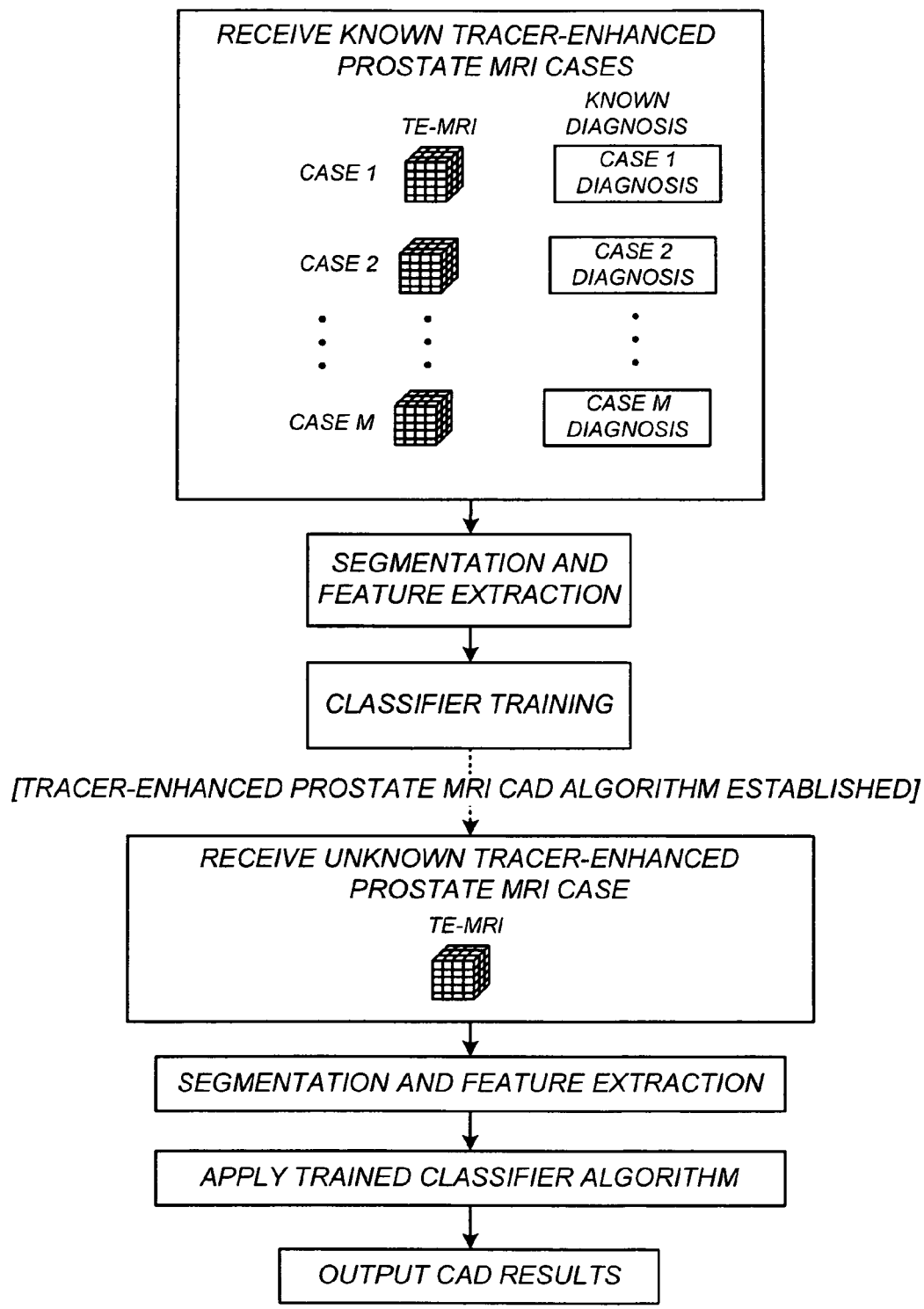
FIG. 17 illustrates CAD for tracer-enhanced prostate MRI image volumes according to a preferred embodiment.

FIG. 17 illustrates computer-aided detection and/or diagnosis (CAD) for tracer-enhanced prostate MRI image volumes according to a preferred embodiment, and which is herein termed tracer-enhanced prostate MRI CAD. The anatomy of the prostate has historically been particularly difficult to image to a degree sufficient for image-based detection of abnormalities. According to a preferred embodiment, a CAD algorithm is designed and applied for a tracer-enhanced volume of the prostate. As illustrated in FIG. 17, training and clinical use of the preferred tracer-enhanced prostate MRI CAD algorithm proceeds in a manner analogous to the above-described prostate MRS CAD algorithm, except that only single, relatively high-resolution tracer-enhanced MRI volumes of the prostate ("TE-MRI") are used.

Figure 18:
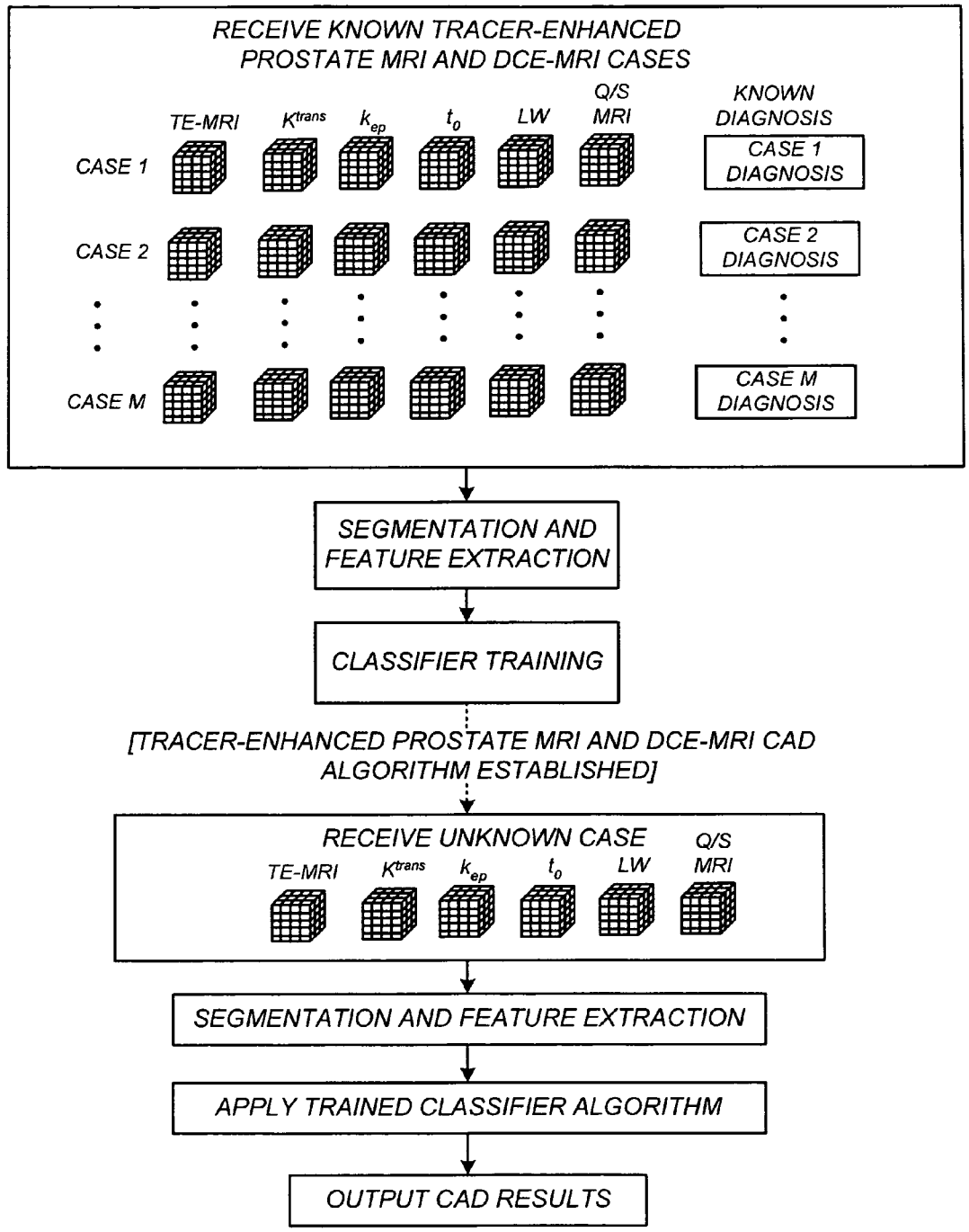
FIG. 18 illustrates combined CAD using tracer-enhanced prostate MRI and DCE-MRI PK parameter information according to a preferred embodiment.

FIG. 18 illustrates computer-aided detection and/or diagnosis (CAD) for the prostate according to a preferred embodiment, wherein both tracer-enhanced prostate MRI (TE-MRI) and DCE-MRI PK parameter information is processed, termed herein prostate TE-MRI/DCE-MRI CAD. As illustrated in FIG. 18, training and clinical use of the preferred prostate TE-MRI/DCE-MRI CAD algorithm proceeds in a manner analogous to the preferred embodiments of FIGS. 15-17, except that both TE-MRI and DCE-MRI volume data are used.

Figure 19:
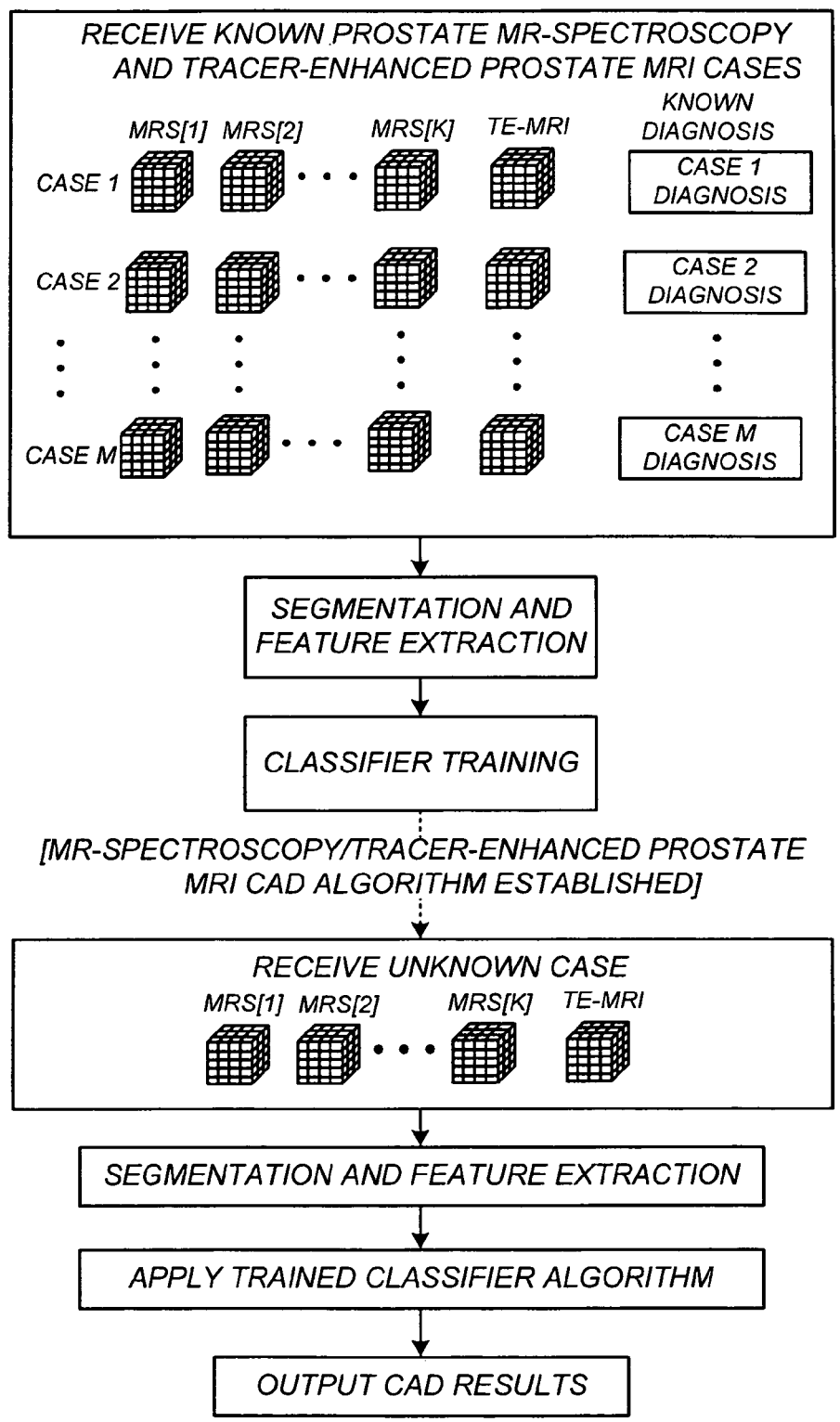
FIG. 19 illustrates combined magnetic resonance spectroscopy (MRS) and tracer-enhanced prostate MRI (TE-MRI) CAD according to a preferred embodiment.

FIG. 19 illustrates computer-aided detection and/or diagnosis (CAD) for the prostate according to a preferred embodiment, wherein both magnetic resonance spectroscopy (MRS) and tracer-enhanced prostate MRI (TE-MRI) and information is processed, termed herein prostate MRS/TE-MRI CAD. As illustrated in FIG. 19, training and clinical use of the preferred prostate MRS/TE-MRI CAD algorithm proceeds in a manner analogous to the preferred embodiments of FIGS. 15-17, except that the MRS and TE-MRI CAD volume data are used.

Figure 20:
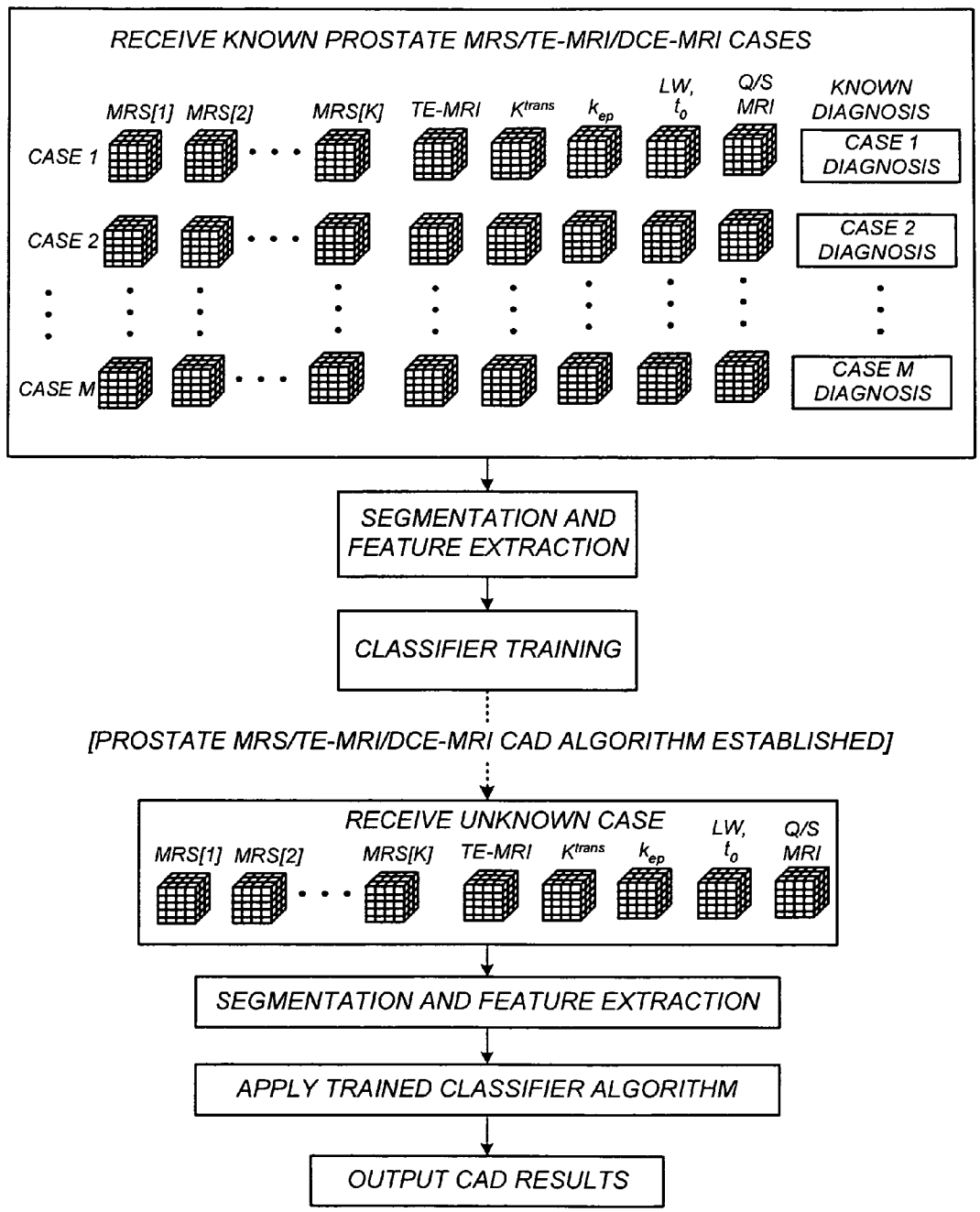
FIG. 20 illustrates combined magnetic resonance spectroscopy (MRS), tracer-enhanced prostate MRI (TE-MRI), and prostate DCE-MRI CAD according to a preferred embodiment.

FIG. 20 illustrates computer-aided detection and/or diagnosis (CAD) for the prostate according to a preferred embodiment, wherein MRS/TE-MRI CAD is further improved by also incorporating the standard DCE-MRI PK parameters $K^{trans}$, $v_e$, $k_{ep}$, and $t_0$ for each voxel. Other PK parameter sets can alternatively be used. As with the preferred embodiment of FIG. 15, supra, it is also within the scope of the preferred embodiments to use an interactive CAD user interface for each of the preferred embodiments of FIGS. 16-20, wherein regions of interest are first identified and/or segmented by the radiologist and then CAD-processed in real time.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although three-dimensional geometric segmentation, feature computation, etc., are described supra for one or more of the preferred CAD methods, it is to be appreciated that such processing in two dimensions (e.g. on a slice-by-slice basis) can be used without departing from the scope of the preferred embodiments. Therefore, reference to the details of the preferred embodiments are not intended to limit their scope, which is limited only by the scope of the claims set forth below.

What is claimed is:

1. A method for dynamic contrast-enhanced magnetic resonance imaging (DCE-MRI) of a body part of a patient to determine a plurality of pharmacokinetic (PK) parameters characterizing a mathematical model-based relationship between a plasma tracer concentration and a total tracer concentration within the body part, comprising:

receiving a plurality of instances of an MRI volume of the body part acquired at a respective plurality of sample times subsequent to an administration of a tracer, said instances comprising voxels of MRI readings timewise variable according to the total tracer concentration but scalewise uncalibrated therewith in that the voxels of MRI readings are not determinative of calibrated absolute values for said total tracer concentration;

for each of said voxels, using a processing system, processing said scalewise uncalibrated MRI readings to compute a first parameter set characteristic of said timewise variations thereof according to a predetermined generalized signal model of a tracer concentration time response, said predetermined generalized signal model being separable between (i) a first subset of generalized signal model parameters determinative of timewise variations of the tracer concentration time response, and (ii) a second subset of generalized signal model parameters determinative of a scale of the tracer concentration time response, said first parameter set corresponding to said first subset of generalized signal model parameters for said MRI readings;

receiving an identification of a calibration region within said MRI volume;

for each of said voxels, processing said scalewise uncalibrated MRI readings against information derived from said identified calibration region to compute a second parameter set characteristic of a scale of said total tracer concentration, said second parameter set corresponding to said second subset of generalized signal model parameters for said total tracer concentration;

receiving an identification of at least one plasma reference region within said MRI volume having known reference PK parameters;

computing a third parameter set characteristic of timewise variations of a representative plasma tracer concentration according to said predetermined generalized signal model and fourth parameter set characteristic of a scale of the representative plasma tracer concentration according to said predetermined generalized signal model based on the first and second parameter sets for locations in the at least one identified plasma reference region and said reference PK parameters therefor; and computing said plurality of PK parameters for each of said voxels using said first, second, third and fourth parameter sets.

2. The method of claim 1, said identification of at least one plasma reference region being an identification of at least one first plasma reference region, the method further comprising:

receiving an identification of at least one second plasma reference region different than said at least one first plasma reference region and having known reference PK parameters;

recomputing said third and fourth parameter sets based on the first and second parameter sets for locations in the at least one second plasma reference region and said reference PK parameters therefor; and recomputing said plurality of PK parameters for each of said voxels using said first parameter set, said second parameter set, and said recomputed third and fourth parameter sets;

whereby said plurality of PK parameters are recomputed based on an identification of at least one different plasma reference region without requiring recomputation of said first and second parameter sets.

3. The method of claim 1, wherein said body part comprises of one of a breast and a prostate, and wherein said at least one plasma reference region comprises one of pectoral muscle tissue and left ventricular volume.

4. The method of claim 3, wherein said at least one plasma reference region comprises at least three separate plasma reference regions.

5. The method of claim 1, said identified calibration region being a first calibration region, the method further comprising:

receiving an identification of a second calibration region within said MRI volume;

for each of said voxels, recomputing said second parameter set by processing said scalewise uncalibrated MRI readings against information derived from said identified second calibration region;

recomputing said fourth parameter set based on said recomputed second parameter sets for locations in the at least one identified plasma reference region and said reference PK parameters therefor; and recomputing said plurality of PK parameters for each of said voxels using said first parameter set, said recomputed second parameter set, said third parameter set, and said recomputed fourth parameter set;

whereby said plurality of PK parameters are recomputed based on an identification of at least one different calibration region without requiring recomputation of said first and third parameter sets.

6. The method of claim 2, wherein said calibration region and said plasma reference region are automatically segmented by computer processing of the MRI volume.

7. The method of claim 2, wherein said calibration region and said plasma reference region are manually identified by a viewer.

8. The method of claim 1, wherein said plurality of pharmacokinetic parameters comprises an extra-cellular tissue volume ratio ($v_e$), a bolus arrival time ($t_0$), and a tracer transfer constant ($K^{trans}$).

9. The method of claim 1, further comprising displaying a map of at least one of said plurality of pharmacokinetic parameters as an overlay to a viewable MRI volume corresponding to said MRI volume.

10. A method for dynamic contrast-enhanced magnetic resonance imaging (DCE-MRI) of a body part of a patient to determine a plurality of pharmacokinetic (PK) parameters characterizing a mathematical model-based relationship between a plasma tracer concentration and a total tracer concentration within the body part, comprising:

receiving a plurality of instances of an MRI volume of the body part acquired at a respective plurality of sample times subsequent to an administration of a tracer, said instances comprising voxels of MRI readings variable according to the total tracer concentration but scalewise uncalibrated therewith in that the voxels of MRI readings are not determinative of calibrated absolute values for said total tracer concentration;

prior to an interactive display session, using a processing system, processing said scalewise uncalibrated MRI readings to compute a first parameter set characteristic of said timewise variations thereof according to a predetermined generalized signal model of a tracer concentration time response, said predetermined generalized signal model being separable between (i) a first subset of generalized signal model parameters determinative of timewise variations of the tracer concentration time response, and (ii) a second subset of generalized signal model parameters determinative of a scale of the tracer concentration time response, said first parameter set corresponding to said first subset of generalized signal model parameters for said MRI readings;

during the interactive display session, receiving a user identification of a calibration region within said MRI volume; and computing said PK parameters for all voxels in said MRI volume using said first parameter set, said uncalibrated MRI readings, and information derived from said identified calibration region within a real time interval after receiving said user identification, comprising:

computing a second parameter set corresponding to said second subset of generalized signal model parameters for said total tracer concentration, said first and second parameter sets forming a total tracer concentration parameter set;

computing a third parameter set characteristic of timewise variations of a representative plasma tracer concentration according to said predetermined generalized signal model and fourth parameter set characteristic of a scale of the representative plasma tracer concentration according to said predetermined generalized signal model based on the first and second parameter sets for locations in at least one identified plasma reference region and a plurality of reference PK parameters associated therewith; and computing said plurality of PK parameters for each of said voxels using said first, and second, third and fourth parameter sets.

11. The method of claim 10, wherein said third and fourth parameter sets forming a plasma tracer concentration parameter set, said generating the third and fourth parameter sets comprising modifying said total concentration parameter set for voxels within said at least one plasma reference region using substantially arithmetic computations, and said computing said plurality of PK parameters for each of said voxels comprising using substantially arithmetic operations on said total concentration parameter set and said plasma concentration parameter set.

12. The method of claim 11, wherein said at least one plasma reference region comprises one of pectoral muscle tissue and left ventricular volume.

13. The method of claim 11, wherein said at least one plasma reference region comprises at least three separate plasma reference regions.

14. The method of claim 10, wherein said body part comprises of one of a breast and a prostate.

15. The method of claim 10, wherein said plurality of pharmacokinetic parameters comprises an extra-cellular tissue volume ratio ($v_e$), a bolus arrival time ($t_0$), and a tracer transfer constant ($K^{trans}$).

16. The method of claim 10, further comprising displaying a map of at least one of said plurality of pharmacokinetic parameters as an overlay to a viewable MRI volume corresponding to said MRI volume.

17. A method for interactive processing and display of dynamic contrast-enhanced magnetic resonance imaging (DCE-MRI) information, comprising:

(i) prior to an interactive user session:

receiving a plurality of instances of an MRI volume of a body part acquired at a respective plurality of sample times subsequent to an administration of a tracer, said instances comprising voxels of MRI readings that are timewise variable according to a total tracer concentration but scalewise uncalibrated therewith in that the voxels of MRI readings are not determinative of calibrated absolute values for said total tracer concentration; and for each of said voxels, using a processing system, processing said scalewise uncalibrated MRI readings to compute a first parameter set characteristic of said timewise variations thereof according to a predetermined generalized signal model of a tracer concentration time response, said predetermined generalized signal model being separable between (i) a first subset of generalized signal model parameters determinative of timewise variations of the tracer concentration time response, and (ii) a second subset of generalized signal model parameters determinative of a scale of the tracer concentration time response, said first parameter set corresponding to said first subset of generalized signal model parameters for said MRI readings;

(ii) receiving an identification of the voxels of the MRI volume corresponding to at least one reference region;

(iii) during the interactive user session:

receiving a first user input determinative of information from which scalewise calibration of the MRI readings with the total tracer concentration can be performed for each voxel;

for each of said voxels, performing said scalewise calibration for at least two of said MRI readings using said first user input;

for each of said voxels, computing a second parameter set using said at least two scalewise calibrated MRI readings, said second parameter set corresponding to said second subset of generalized signal model parameters for said total tracer concentration; and for each of said voxels lying outside the at least one reference region, computing each of said plurality of PK parameters using (a) said first and second parameter sets for that voxel, and (b) representative first and second parameter sets for said identified voxels in said at least one reference region, said representative first parameter set being characteristic of timewise variations of a representative plasma tracer concentration according to said predetermined generalized signal model and said representative second parameter set being characteristic of a scale of the representative plasma tracer concentration according to said predetermined generalized signal model, said representative first and second parameter sets being based on said first and second parameter sets for locations in at least one identified plasma reference region and a plurality of reference PK parameters associated therewith;

wherein said performing said scalewise calibration, said computing the second parameter set, and said computing each of said plurality of PK parameters are of minor computational intensity compared to said computing the first parameter set and are performed in a real-time interval across all of said voxels during said interactive user session.

18. The method of claim 17, wherein said body part comprises of one of a breast and a prostate.

19. The method of claim 17, wherein said plurality of pharmacokinetic parameters comprises an extra-cellular tissue volume ratio ($v_e$), a bolus arrival time ($t_0$), and a tracer transfer constant ($K^{trans}$).

20. The method of claim 17, further comprising displaying a map of at least one of said plurality of pharmacokinetic parameters as an overlay to a viewable MRI volume corresponding to said MRI volume.

* * * * *